(12) United States Patent
Agee et al.

(10) Patent No.: US 8,246,561 B1
(45) Date of Patent: Aug. 21, 2012

(54) SYSTEMS, DEVICES AND METHODS FOR TREATING ACUTE DORSAL FRACTURE DISLOCATIONS OF THE PIP JOINT

(75) Inventors: John M. Agee, Cameron Park, CA (US); Jeffrey Woodhouse, Sacramento, CA (US); Michael Swanstrom, Davis, CA (US); Francis C. King, Sacramento, CA (US)

(73) Assignee: John M. Agee, Sacramento, CA (US), Trustee of the John M. Agee Trust of Aug. 15, 1996

( * ) Notice: Subject to any disclaimer, the term of this patent is extended or adjusted under 35 U.S.C. 154(b) by 315 days.

(21) Appl. No.: 11/834,914

(22) Filed: Aug. 7, 2007

(51) Int. Cl.
*A61F 5/00* (2006.01)
*A61F 2/46* (2006.01)
*A61G 15/00* (2006.01)
*A61B 17/00* (2006.01)

(52) U.S. Cl. ............. 602/22; 128/845; 602/36; 602/32; 606/54; 606/57; 606/59; 606/86 R

(58) Field of Classification Search .............. 602/22, 602/21, 36, 32, 20; 128/845, 880; 606/54, 606/55, 57, 59, 58, 86 R
See application file for complete search history.

(56) References Cited

U.S. PATENT DOCUMENTS

| | | | |
|---|---|---|---|
| 6,565,563 B1 * | 5/2003 | Agee et al. ............ | 606/55 |
| 2005/0085810 A1 * | 4/2005 | Lutz et al. ............ | 606/54 |

* cited by examiner

*Primary Examiner* — Patricia Bianco
*Assistant Examiner* — Victoria J Hicks
(74) *Attorney, Agent, or Firm* — John P. O'Banion

(57) ABSTRACT

Systems, device and methods are described for maintaining concentric reduction of the proximal interphalangeal (PIP) joint of a finger with few as two orthopedic pins, one inserted through the head of the proximal phalanx concentric with the axis of rotation of the joint (i.e., a transverse pin), and the other through the middle phalanx at a location between the PIP and distal interphalangeal (DIP) joint (a dorsal pin), and applying a force between the two pins. A surgical kit is described which may include such components as a dorsal pin, a transverse pin, a pin placement guide for use in reducing the joint fracture dislocation and then drilling holes for the pins or for inserting self-drilling pins, and a fixation device for coupling and applying a force between the dorsal and transverse pins. The components of the surgical kit are described, including various configurations of the fixation device.

29 Claims, 23 Drawing Sheets

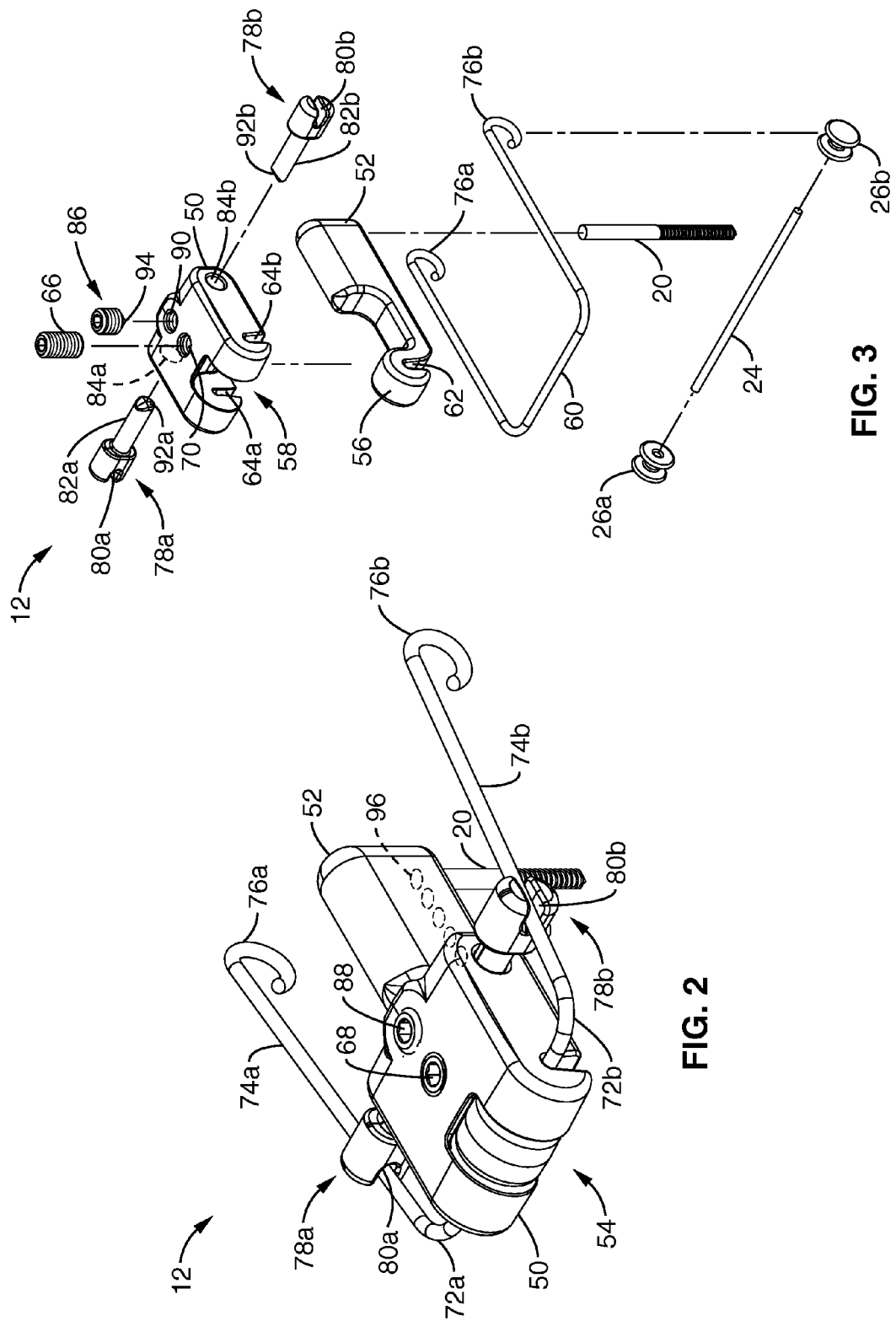

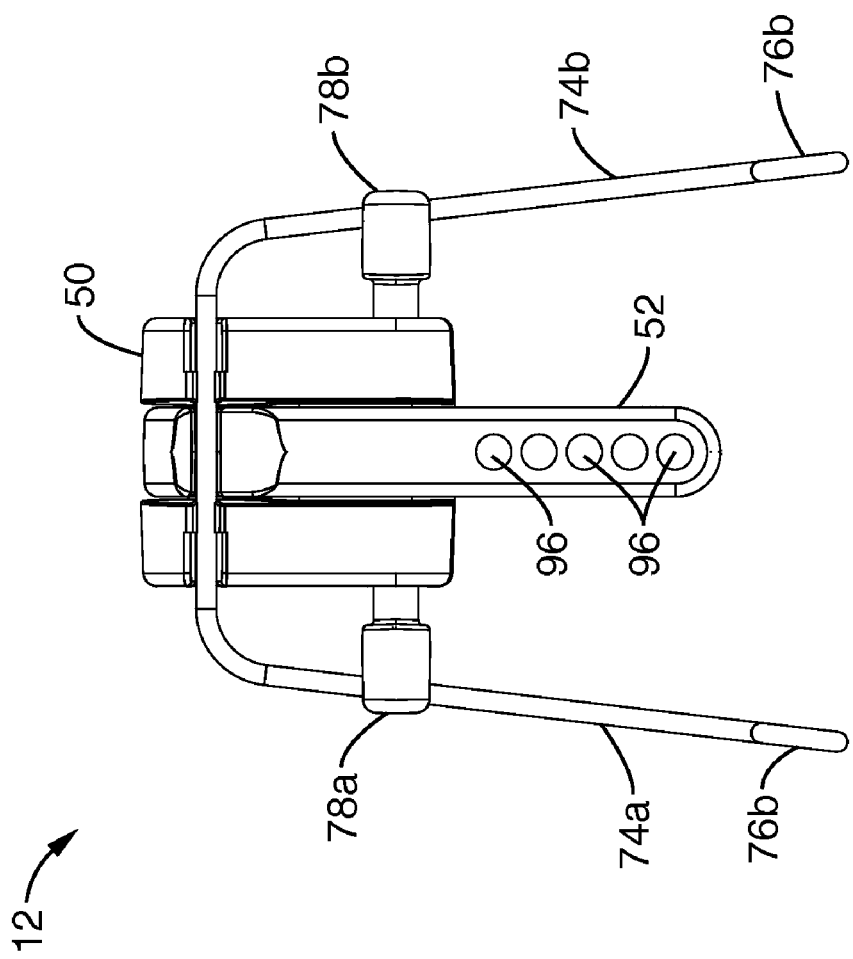

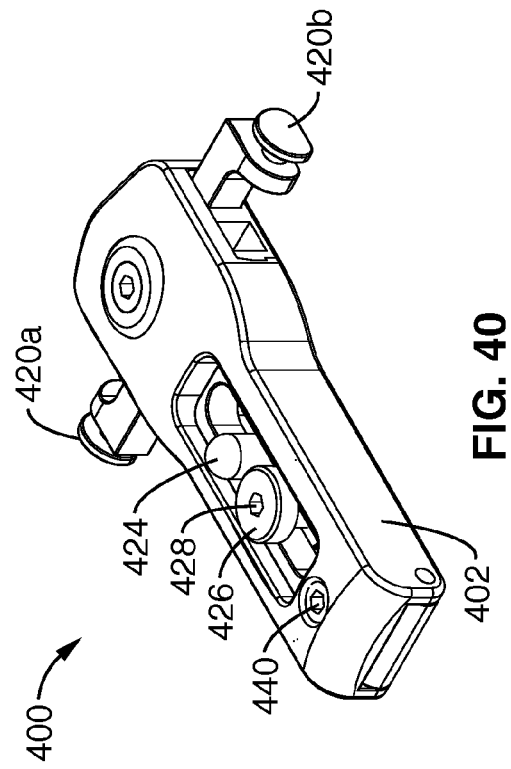
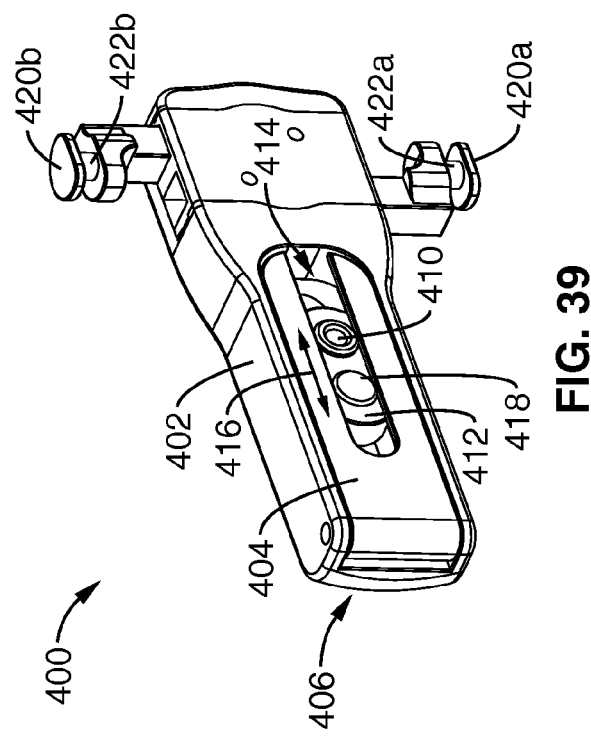

SYSTEMS, DEVICES AND METHODS FOR TREATING ACUTE DORSAL FRACTURE DISLOCATIONS OF THE PIP JOINT

CROSS-REFERENCE TO RELATED APPLICATIONS

Not Applicable

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

This invention pertains generally to treatment of injuries of a skeletal joint and, more particularly, to systems, devices and methods for treatment of acute dorsal fracture dislocations of the proximal interphalangeal (PIP) joint in a finger.

2. Description of Related Art

Proximal interphalangeal joint fractures frequently have associated subluxations and/or dislocations of the middle phalanx with respect to the head of the proximal phalanx. Increasing degrees of joint injury are associated with increased degrees of joint instability. Injuries that feature dorsal displacement of the base of the middle phalanx on the head of the proximal phalanx frequently require skeletal fixation to obtain fracture and joint surface realignment. In addition, there are advantages with techniques that can obtain and maintain fracture and joint alignment by a dynamic force that will permit active range of motion while the bone and soft tissues heal. These active range of motion exercises (i.e., the patient's own muscles moving the injured joint through flexion and extension arcs of motion) serve to minimize joint stiffness and optimize the final result.

To achieve proper healing, a dynamic splint should maintain concentric joint reduction; specifically anatomic alignment of the articular base of the middle phalanx with respect to the head of the proximal phalanx such that rotation of the middle phalanx on the proximal phalanx occurs strictly about the anatomic axis of rotation of the PIP joint. When concentric joint reduction is not maintained, gliding motion between the intact dorsal base of the middle phalanx with respect to the head of the proximal phalanx is lost. The resultant rocking joint motion progressively destroys the articular joint cartilage, which produces pain, stiffness and increasingly severe degrees of traumatic arthritis.

One approach to addressing the foregoing concerns involves the use of what is referred to in the medical profession as a "force couple splint" which uses two Kirschner wires ("K-wires") inserted transversely through the phalanxes in combination with a dorsal pin. In this approach, one K-wire is inserted through the middle phalanx, one K-wire is inserted through the proximal phalanx, and a dorsal pin is inserted into the middle phalanx. Once the K-wires are inserted, the protruding ends of both wires are bent at right angles in an interlocking arrangement, and an elastic band is deployed between the upturned ends of one K-wire and the exposed end of the dorsal pin. The "force couple" that is achieved by this construction is the combination of two coupled forces, one acting as a lever to the middle phalanx to urge the base of the middle phalanx in the palmar direction, and the other urging the distal end of the proximal phalanx in the dorsal direction.

While a "force couple splint" as described above provides a satisfactory solution, placement and insertion of the K-wires can be challenging for the surgeon. The placement and insertion procedure can be both complex and time-consuming, both of which are further considerations for which a solution is needed.

BRIEF SUMMARY OF THE INVENTION

Accordingly, an aspect of the present invention is to reduce the complexity associated with use of a conventional force couple splint while retaining the advantages of that type of fixation device. Another aspect of the invention is to reduce the number of pins or wires that are required to be placed for proper force couple treatment of PIP joint injuries. An absence of the need for K-wires, or the reduction in number of K-wires or pins which require placement, leads to another aspect of the invention which is a reduction in the amount of manipulation (i.e., angular bending) of the wires or pins required subsequent to their insertion into the bones.

According to a further aspect of the invention, PIP joint injuries can be treated with as few as two pins (e.g., a dorsal pin and a transverse pin) and yet still provide sufficient force coupling to achieve proper healing of the injured joint. Another aspect of the invention is that concentric reduction of the PIP joint is maintained through a wide angular range of joint rotation.

Still another aspect of the invention is a treatment method that involves the insertion of a single pin through the head of the proximal phalanx concentric with the axis of rotation of the joint (referred to herein as a "transverse pin"), together with the insertion of a single pin in the dorsal side of the middle phalanx between the PIP and DIP joints (referred to herein as a "dorsal pin"). The dorsal pin is drilled from dorsal to palmar to engage both cortices of this tubular bone, and its cutting tip does not extend palmar to the bone so as to avoid injury to the flexor tendons. The term "transverse pin" is used herein to denote the pin that is inserted through the head of the proximal phalanx, since this pin once inserted will be transverse to both proximal and middle phalanxes. Likewise, the term "dorsal pin" is used to denote the pin that is inserted in the middle phalanx, since this pin is inserted from the dorsal side in the dorsal to palmar direction.

Another aspect of the invention is a "fractured finger fixation" or "F3" device. This device is configured such that, once the pins are inserted, the device can be mounted to the pins in a manner that will apply force to the dorsal pin, and hence to the proximal end of the middle phalanx, in a palmar direction while simultaneously applying force to the transverse pin, and hence the distal end of the proximal phalanx, in the dorsal direction.

While the performance of the foregoing method is not limited to any particular fixation device construction, another aspect of the invention is a variously embodied fixation device characterized by a single support member or, preferably, two support members joined together by an adjustable connection. A set of tension connectors in the form of hooks or the like is coupled to one of the support members with one such connector on each side, and the other support member is configured for coupling to the dorsal pin. Another set of tension connections in the form of end caps or the like are coupled to the transverse pin with one such connector on each end of the pin. An elastic band on each side of the device is coupled between the tension connectors on the device and the tension connectors on the transverse pin to apply a translational force between the dorsal pin and the transverse pin. Adjustability of the relative position between the two support members controls the amount of force applied. This force translates the intact dorsal base of the middle phalanx in a palmar direction as it simultaneously lifts the head of the proximal phalanx in a dorsal direction.

According to an aspect of the invention, the fixation device configuration is defined in terms of three substantially orthogonal directions of adjustment. The tension connectors are spaced apart along one of the directions, the spacing between the two support members is variable along the second direction, and the distance between the dorsal pin and the plane established by the tension connectors is along the third direction.

Further to the foregoing aspect of the invention, the two tension connectors on the device are spaced to engage the two tension connectors on the transverse pin, and the direction of separation between them is referred to herein as a first horizontal direction. In certain embodiments of the invention, the separation of the two tension connectors on the device is variable along this first horizontal direction to accommodate fingers of different widths. In certain embodiments, the adjustable connection between the support members is either a pivot connection, in which case the distance between them is varied by varying the pivot angle, or a linear connection of variable length, in which case the distance between them is varied by extending or contracting the length. In either case, the direction along which the distance varies is referred to herein as a vertical direction, although movement along this direction can be achieved by either a pivoting movement or a strictly linear movement, depending on the type of connection between the two support members.

The support member configured to be coupled to the dorsal pin is further configured to receive the dorsal pin in an orientation substantially parallel to the vertical direction. Finally, the distance separating the dorsal pin and the first horizontal direction is referred to herein as a second horizontal direction. In certain embodiments of this invention, this distance can be varied to accommodate fingers of different lengths.

Variation of the distance between the two support members will cause the dorsal set of tension connectors to rise or fall along a vertical direction relative to the finger (i.e., dorsal-palmar direction), and thereby increase or decrease the opposing forces applied to the transverse and dorsal pins. This in turn varies the forces applied to the head of the proximal phalanx and the proximal end of the middle phalanx, respectively.

Still further, an aspect of the present invention is a pin placement guide configured to reduce the fracture dislocation and then facilitate drilling passages in the proximal and middle phalanges and insertion of the transverse and dorsal pins.

A further aspect of the invention is a cap applicator device configured for facilitating compressing tension connectors onto the ends of the transverse pin.

A still further aspect of the invention is a spacer device configured to facilitate cutting the dorsal and transverse pins to the correct length.

Another aspect of the invention is the provision of a system or kit comprising the F3 device, the pin placement guide, the cap applicator, the spacer device, pin caps, a dorsal pin, a drill bit for the dorsal pin, and a self-drilling transverse pin.

An aspect of the invention is an apparatus for repositioning the middle phalanx of a finger in relation to the head of the proximal phalanx in said finger where said finger has an associated proximal interphalangeal joint fracture dislocation.

In one embodiment, the apparatus comprises a support member adapted for coupling to a dorsal pin positioned in the middle phalanx of the finger and further adapted for coupling to a single transverse pin positioned in the proximal phalanx of the finger; and means for exerting a force between the dorsal and transverse pins which simultaneously translates the middle phalanx in a palmar direction and the head of the proximal phalanx in a dorsal direction.

In another embodiment, the apparatus comprises a first support member; a second support member pivotally coupled to the first support member and adapted for coupling to a dorsal pin positioned in said middle phalanx of said finger, where the first and second support members are adapted for relative articulation through an angle; means for adjusting the relative angle between the first and second support members; a U-shaped rod coupled to at least one of the support members, the rod having a pair of arms with a tension connector at each end, each tension connector adapted for coupling a tension generating element to a single transverse pin positioned in the proximal phalanx of the finger; and means coupled to the first support member for adjusting the relative distance between the tension connectors, wherein the apparatus is adapted to exert a force between the dorsal and transverse pins which simultaneously translates the middle phalanx in a palmar direction and the head of the proximal phalanx in a dorsal direction.

In another embodiment, the apparatus comprises a first support member; a second support member coupled to the first support member, wherein the first and second support members are adapted for relative articulation through an angle; means for adjusting the relative angle between the first and second support members; a transverse arm assembly coupled to the first support member; a pair of tension connectors coupled to the transverse arm assembly; and means for adjusting relative distance between said tension connectors; each tension connector adapted for coupling a tension generating element to a single transverse pin positioned in said proximal phalanx of said finger; the second support member being adapted for coupling to a dorsal pin positioned in said middle phalanx of said finger; wherein the apparatus is adapted to exert a force between the dorsal and transverse pins which simultaneously translates the middle phalanx in a palmar direction and the head of the proximal phalanx in a dorsal direction.

In still another embodiment, the apparatus comprises first and second support members joined to each other by adjustable connecting means for orienting the support members with an adjustable spacing therebetween along a direction defined as a vertical direction; first and second tension connectors coupled to the first support member and spaced from each other along a direction that is transverse to the vertical direction and which is defined as a first horizontal direction; and pin receiving means in the second support member for receiving a dorsal pin in an orientation substantially parallel to said vertical direction and spaced apart from the first and second tension connectors along a second horizontal direction that is substantially perpendicular to both said vertical direction and said first horizontal direction; whereby the adjustable connecting means is configured to adjust the position of the first and second tension connectors along said vertical direction relative to said the receiving means.

Another aspect of the invention is an apparatus for preparing a finger having an associated proximal interphalangeal joint fracture dislocation for deployment of a fixation device.

In one embodiment, the apparatus comprises means for receiving the finger and reducing the proximal interphalangeal joint; means for guiding insertion of a transverse pin in the head of the proximal phalanx of the finger after the joint is reduced; and means for guiding insertion of a dorsal pin in the middle phalanx of the finger after the joint is reduced.

Another aspect of the invention is an apparatus for reducing a joint in a finger having an associated proximal interphalangeal joint fracture dislocation, and for guiding the placement of pins for deployment of a fixation device.

In one embodiment, the apparatus comprises a palmar beam; a dorsal beam; means for slidably coupling the beams to each other in a substantially parallel orientation; a distal palmar block slidably coupled to the palmar beam for movement along the palmar beam in a proximal-distal direction; a proximal palmar block integrated into the palmar beam; a dorsal block integrated into the dorsal beam; a dorsal drill guide tube slidably coupled to the dorsal beam; a transverse pin guide coupled to the dorsal beam; a transverse pin guide tube coupled to the transverse pin guide; means for adjusting the position of the transverse pin guide tube in a palmar-dorsal direction; means for adjusting the position of the transverse pin guide tube along the dorsal beam in a proximal-distal direction; and means for adjusting the position of the dorsal drill guide tube along the dorsal beam in a proximal-distal direction.

In another embodiment, the apparatus comprises a palmar beam; a dorsal beam; means for slidably coupling the beams to each other in a substantially parallel orientation; a distal palmar block slidably coupled to the palmar beam for movement along the palmar beam in a proximal-distal direction; a proximal palmar block integrated into the palmar beam; a dorsal block integrated into the dorsal beam; a dorsal drill guide block slidably coupled to the dorsal beam; a dorsal drill guide tube coupled to the dorsal drill guide block; the dorsal drill guide block being adapted for adjustment of the dorsal drill guide tube along the dorsal beam between the palmar blocks; a height adjustment block having a lower member slidably coupled to the dorsal beam and an upper member slidably coupled to the lower member; a transverse pin guide coupled to the upper member of the height adjustment block; a transverse pin guide tube coupled to the transverse pin guide; a screw mechanism coupled to the upper member of the height adjustment block and adapted for adjusting the relative position between the upper member and the lower member; and a screw mechanism coupled to the dorsal beam and adapted for adjusting the position of the lower member of the height adjustment block along the dorsal beam in the proximal-distal direction.

In another embodiment, the apparatus comprises a palmar beam including first and second blocks spaced apart from each other along said palmar beam, each of the first and second blocks having a palmar-facing surface; a dorsal beam having a third block a dorsal-facing surface; a dorsal drill guide tube extending through the third block and oriented in a direction extending from the dorsal beam toward the palmar beam; a transverse pin guide tube; means for coupling the transverse pin guide tube to the dorsal beam wherein the transverse pin guide tube is oriented in a direction transverse to the dorsal drill guide tube; means for coupling the palmar and dorsal beams in a spaced-part and substantially parallel orientation; means for varying the spacing between the beams; means for varying the position of the dorsal drill guide tube along the dorsal beam; means for varying the position of the transverse pin guide tube along the dorsal beam; and means for varying the position of the transverse pin guide tube in a palmar-dorsal direction.

Another aspect of the invention is a surgical kit for use in treating a dislocation of the middle phalanx of a finger in relation to the distal end of the proximal phalanx in the finger where the dislocation is a proximal interphalangeal (PIP) joint fracture dislocation.

In one embodiment, the kit comprises a pin placement guide adapted to reduce the fracture and hold it in a reduced anatomic position wherein a dorsal bone pin can be inserted into the middle phalanx and a transverse bone pin can be inserted into the distal end of the proximal phalanx through the axis of PIP joint rotation; and an external skeletal fixator adapted to obtain and maintain concentric reduction of the PIP joint, wherein the fixator exerts a volarly or palmarly translating force on the middle phalanx and exerts a dorsally translating force to the distal end of the proximal phalanx to restore joint alignment; wherein the fixator is adapted for coupling to a single transverse bone pin.

In another embodiment, the kit comprises a dorsal bone pin; a transverse bone pin; a pin placement guide adapted to reduce the fracture and hold it in a reduced anatomic position wherein the dorsal bone pin can be inserted into the middle phalanx and the transverse bone pin can be inserted into the distal end of the proximal phalanx through the axis of PIP joint rotation; an external skeletal fixator adapted to obtain and maintain concentric reduction of the PIP joint, wherein the fixator exerts a volarly or palmarly translating force on the middle phalanx and exerts a dorsally translating force to the distal end of the proximal phalanx to restore joint alignment; and a plurality of elastic bands; wherein the fixator is adapted to be coupled to a single transverse bone pin using the elastic bands as linkage.

In a further embodiment, the kit comprises a dorsal bone pin; a pre-drill bit for the dorsal bone pin; a self-drilling transverse bone pin; a pin placement guide adapted to reduce the fracture and hold it in a reduced anatomic position while a hole in the middle phalanx is drilled using the pre-drill bit and the dorsal bone pin is inserted into the hole, and while said transverse bone pin is inserted into the distal end of the proximal phalanx through the axis of PIP joint rotation; an external skeletal fixator adapted to obtain and maintain concentric reduction of the PIP joint, wherein the fixator exerts a volarly or palmarly translating force on the middle phalanx and exerts a dorsally translating force to the distal end of the proximal phalanx to restore joint alignment; and a plurality of elastic bands; wherein said fixator is adapted to be coupled to a single said transverse bone pin using the elastic bands as linkage.

Another aspect of the invention is a method for fixation of a fracture dislocation at a proximal interphalangeal joint, said proximal interphalangeal joint defined as a joint at which a proximal phalanx is joined to a middle phalanx at the head of said proximal phalanx and that has an axis of rotation at said head of said proximal phalanx, each said phalanx having proximal and distal ends and dorsal and palmar sides, the method comprising inserting a dorsal pin through said middle phalanx in a dorsal-to-palmar direction; either before or after the foregoing step, inserting a single transverse pin through said head of said proximal phalanx concentric with said axis of rotation; and with said dorsal and transverse pins so inserted, connecting said dorsal and transverse pins through a common fixation device adapted to simultaneously (i) apply force to said dorsal pin to urge said proximal end of said middle phalanx in a palmar direction, and (ii) apply force to said transverse pin to urge said distal end of said proximal phalanx in a dorsal direction, and to maintain both said forces during flexion and extension of said proximal interphalangeal joint.

In another embodiment, the method comprises inserting a dorsal pin through an approximate midpoint of the middle phalanx in a dorsal-to-palmar direction; securing the dorsal pin against dorsal-to-palmar movement in the middle phalanx; inserting a single transverse pin through the head of the proximal phalanx concentric with the axis of rotation; and with the dorsal and transverse pins so inserted, connecting the dorsal and transverse pins through a common fixation device adapted to simultaneously (i) apply force to the dorsal pin to urge the proximal end of the middle phalanx in a palmar direction, and (ii) apply force to the transverse pin to urge said distal end of said proximal phalanx in a dorsal direction, and to maintain both said forces during flexure of said proximal interphalangeal joint.

It will be appreciated, therefore, that the present invention provides beneficial systems, devices and methods for treatment of a fracture in the PIP joint.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIG. 2 is perspective view of a fractured finger fixation (F3) device according to the present invention.

FIG. 3 is an exploded perspective view of the device shown in FIG. 2.

FIG. 4 is a bottom plan view of the device shown in FIG. 2.

FIG. 39 is a bottom perspective view of the device shown in FIG. 37, illustrating a sliding receptacle for insertion of the dorsal pin to adjust the longitudinal position between the dorsal pin and the transverse pin.

FIG. 40 is a top perspective view of the device shown in FIG. 37.

DETAILED DESCRIPTION OF THE INVENTION

Figure 1:
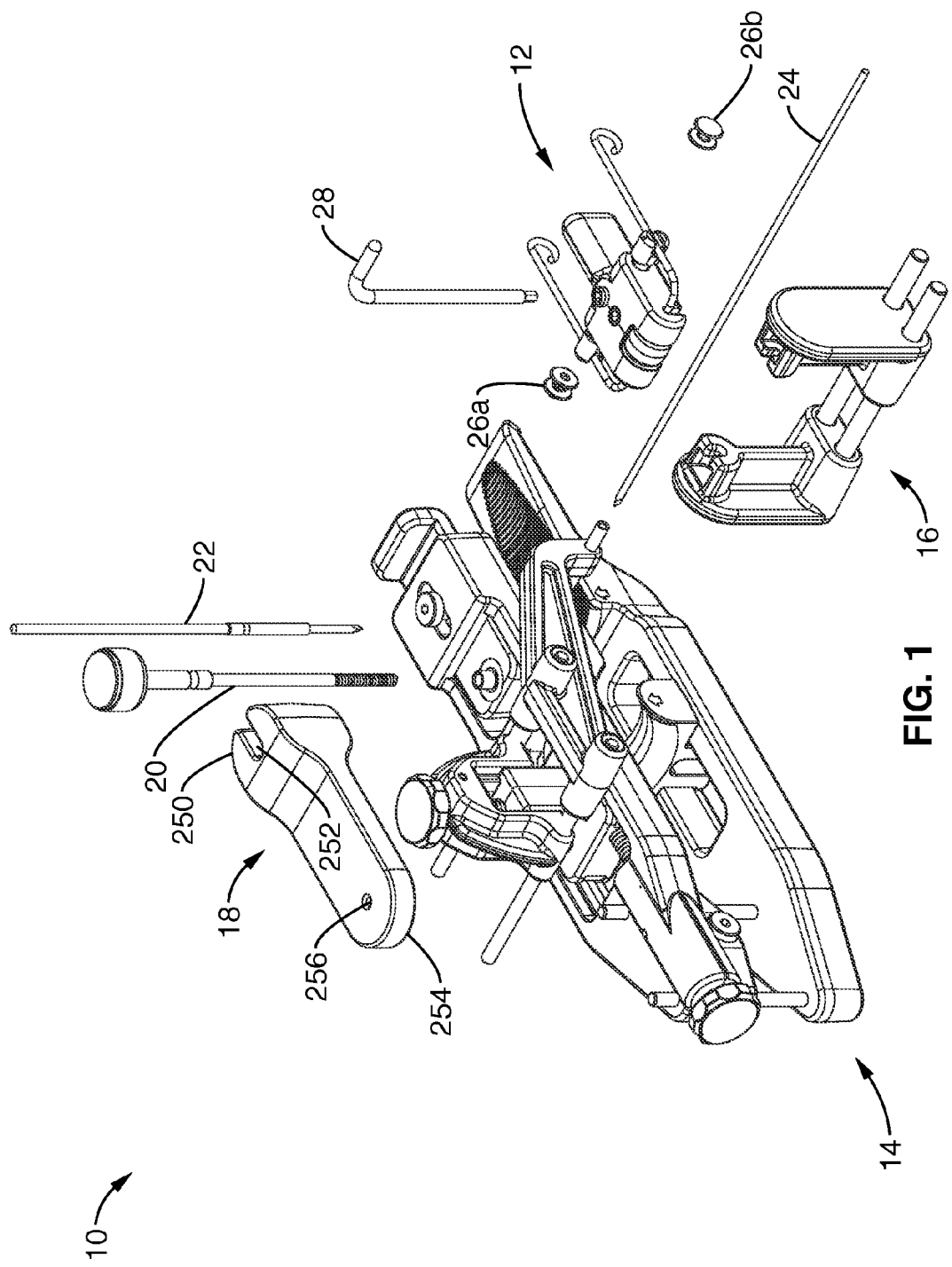
FIG. 1 is a perspective view of an embodiment of a surgical system or kit for treatment of a PIP joint fracture according to the present invention.

Various embodiments of the present invention will now be described with reference to FIG. 1 through FIG. 46 of the drawings. It will be appreciated that the system(s), device(s) and method(s) described herein represent exemplary embodiments and that the invention is intended to encompass other embodiments that will become apparent to one of ordinary skill in the art from the description herein.

To facilitate understanding the invention, certain terms are used herein to refer to anatomical features and characteristics of the hand and fingers. It is intended that those terms be given their plain meaning except as otherwise defined herein.

For example, the term "palmar" as used herein, when describing a direction, denotes the direction perpendicular to the palm, through the hand and toward the palm. Thus, when the hand is held with palm is facing downward, the palmar direction is downward. The term "palmar" is also used herein to denote the pad side of a finger, that is, the side that is on the same side of the hand as the palm when the fingers are outstretched, the palmar direction extending from the nail side through the finger to the finger pad. The term "dorsal" as used herein, when describing a direction, denotes the direction opposite to the palmar direction, that is, from the palm through the hand to the back of the hand, and likewise through the finger from the finger pad to the nail side, i.e., the side of the finger opposite the finger pad. The term "dorsal" is also used herein to denote the side of the finger opposite the pad side. The term "palmar-dorsal," when describing a direction, denotes the direction perpendicular to the palm when the palm is flattened, and when describing a distance, denotes a distance along that direction. The terms "palmar" and "dorsal" are also used to denote the relative positions of components that are spaced apart in the palmar-dorsal direction, "palmar" denoting the component furthest in the palmar direction, and "dorsal" denoting the component furthest in the dorsal direction.

The terms "proximal" and "distal" are used herein to denote directions along an outstretched finger toward and away from the palm, respectively. The term "proximal-distal" when describing a distance or spacing denotes a distance or spacing along either the proximal or distal direction. "Proximal" and "distal" likewise denote the relative positions of mechanical components or anatomical portions that are spaced apart in the proximal-distal direction, "proximal" denoting the component or portion furthest in the proximal direction, and "distal" denoting the component or portion furthest in the distal direction. The term "longitudinal" when describing a distance of spacing along a structure denotes a distance or spacing along the axis of the structure.

The term "finger-contoured" as used herein when describing a surface of a structure denotes a surface that has a concave curvature to oppose the convex curvature of a surface of a finger and thereby prevent the finger from disengaging the surface when the surface is pressed against the finger. A finger-contoured surface on a structure will in many embodiments of this invention have a radius of curvature sufficiently large to accommodate patients with fingers of different sizes.

The term "a" or "an" is intended to mean "one or more." The term "comprising" when preceding the recitation of a step or an element is intended to mean that the addition of further steps or elements is optional and not excluded.

While the features and principles that characterize this invention and distinguish it over the prior art may be implemented in a variety of ways and embodied in a variety of constructions, these features and principles as applied to the entire invention can be understood by examination of specific examples. The figures herein illustrate such examples.

Referring now to the figures, FIG. 1 illustrates an embodiment of a surgical kit 10 for use in treating acute dorsal fracture dislocations of the proximal interphalangeal (PIP) joint. In the embodiment shown, one component of the kit comprises a fractured finger fixation device 12, also referred to herein as an "F3" device. The kit also comprises a pin placement guide 14, a cap applicator 16, a pin spacer 18, a dorsal bone pin 20, a pre-drill bit 22 for the dorsal pin, a self-drilling transverse bone pin 24, end caps 26a, 26b for the transverse pin, and a hex wrench 28. The kit further comprises a plurality of non-latex elastic bands which are not shown in FIG. 1, but which are shown in other figures and described in detail below. The foregoing components are beneficially included as part of a complete surgical kit, but can also be utilized as standalone devices or combined in various ways as alternative kits or subkits. Additional components can be included as well.

The F3 device 12, which serves as the primary component of the surgical kit, is an external skeletal fixator designed to obtain and maintain concentric reduction of an acute, unstable dorsal fracture subluxation or dislocation of the PIP joint. This device exerts a volarly or palmarly translating force on the middle phalanx and exerts a dorsally translating force to the distal end of the proximal phalanx to restore and maintain joint alignment. With the dorsal dislocation of the middle phalanx reduced, the fractured fragments of the joint surface are reopposed. The effect of the F3 device is present throughout the complete range of finger motion allowing full active flexion and extension during healing of the bone and soft tissues.

The pin placement guide 14 is used to reduce the fracture and hold it in a reduced anatomic position so that the dorsal bone pin 20 can be accurately inserted into the middle phalanx and the transverse bone pin 24 can be accurately placed through the axis of PIP joint rotation. Once the dorsal and traverse pins are inserted, the F3 device is installed on the dorsal pin and is linked to the transverse pin with two elastic bands. These bands provide the translating force that holds the joint concentrically reduced and are preferably positioned substantially perpendicular to the plane of the finger. A tension adjustment screw on the F3 device allows the amount of tension provided by the elastic bands to be "fine tuned" so that the force needed to maintain a concentric joint reduction is exerted. Tension can also be adjusted by increasing the number of elastic bands or by using elastic bands with different elasticity factors either alone or in combination with the tension adjustment screw. Note that the F3 device only requires the use of a single transverse pin; namely, a transverse pin in the head of the proximal phalanx. No transverse pin is required in the middle phalanx as in other devices and techniques, which is a significant advantage over other devices and techniques.

Except for the elastic bands and wrench, the various components of the surgical kit are preferably manufactured from metal and/or plastic materials that can be sterilized. The dorsal and transverse bone pins are preferably fabricated from "316 L" stainless steel or the like. All of the components are preferably disposable and designed for single use only.

Referring now to FIG. 2 through FIG. 4, an exemplary embodiment of an F3 device 12 is illustrated. In the embodiment shown, the F3 device includes a first support member 50 and second support member 52 which is adapted to be coupled to the dorsal pin 20. First support member 50 and second support member 52 are pivotally coupled at a joint 54 which allows for relative articulation of those components. Joint 54 comprises the combination of a hook 56 which is inserted into a recess 58 and a rod 60 which is inserted into recesses 62, 64a, 64b and thereby coupled to the assembly. The relative angle between the first support member and second support member is adjusted by a tension adjustment screw 66, shown here with a hexagonal socket 68, which fits into a threaded aperture 70.

In the embodiment shown, rod 60 is a resilient rod bent at approximate right angles at two locations 72a, 72b into a U-shaped structure with arms 74a, 74b terminating in hook-shaped tension connectors 76a, 76b at each end. A pair of spreaders 78a, 78b is provided with slots 80a, 80b at their outer ends adapted for receiving arms 74a, 74b. The spreaders have arms 82a, 82b which are slidably coupled to first support member 50 by means of apertures 84a, 84b. The relative distance between the outer ends of spreaders 78a, 78b (e.g., width) is adjusted by a set screw 86, shown here with a hexagonal socket 88, which fits into a threaded aperture 90. Spreaders 78a, 78b have angled inner ends 92a, 92b and width adjustment screw 86 has a conically-tapered tip 94. The conically-tapered tip 94 contacts the surfaces of the angled inner ends 92a, 92b of the spreaders such that turning width adjustment screw 86 causes the tip to retract into first support member 50 and move spreaders 78a, 78b apart. As a result, the spreaders push apart the two arms 74a, 74b, thereby varying the spacing between hooks 76a, 76b. When width adjustment screw 86 is turned in the opposite direction, the tip of width adjustment screw 86 is rotated outward from first support member 50 and the resilience (e.g., spring force) of arms 74a, 74b urges spreaders 78a, 78b back toward each other. Thus, the spacing between hooks 76a, 76b is increased or decreased by turning width adjustment screw 86 in one direction or the other. Dorsal pin 20 is connected at its upper end to the underside of second support member 52 at any of several apertures 96 which allow for different degrees of spacing between the dorsal and transverse pins, and thus fingers of different lengths. Rod 60 exerts a palmar-to-dorsal force on transverse pin 24 by tension generating elements (e.g., elastic bands) that loop around the end caps 26a, 26b on the transverse pin and the hooks 76a, 76b of the resilient rod.

Figure 5:
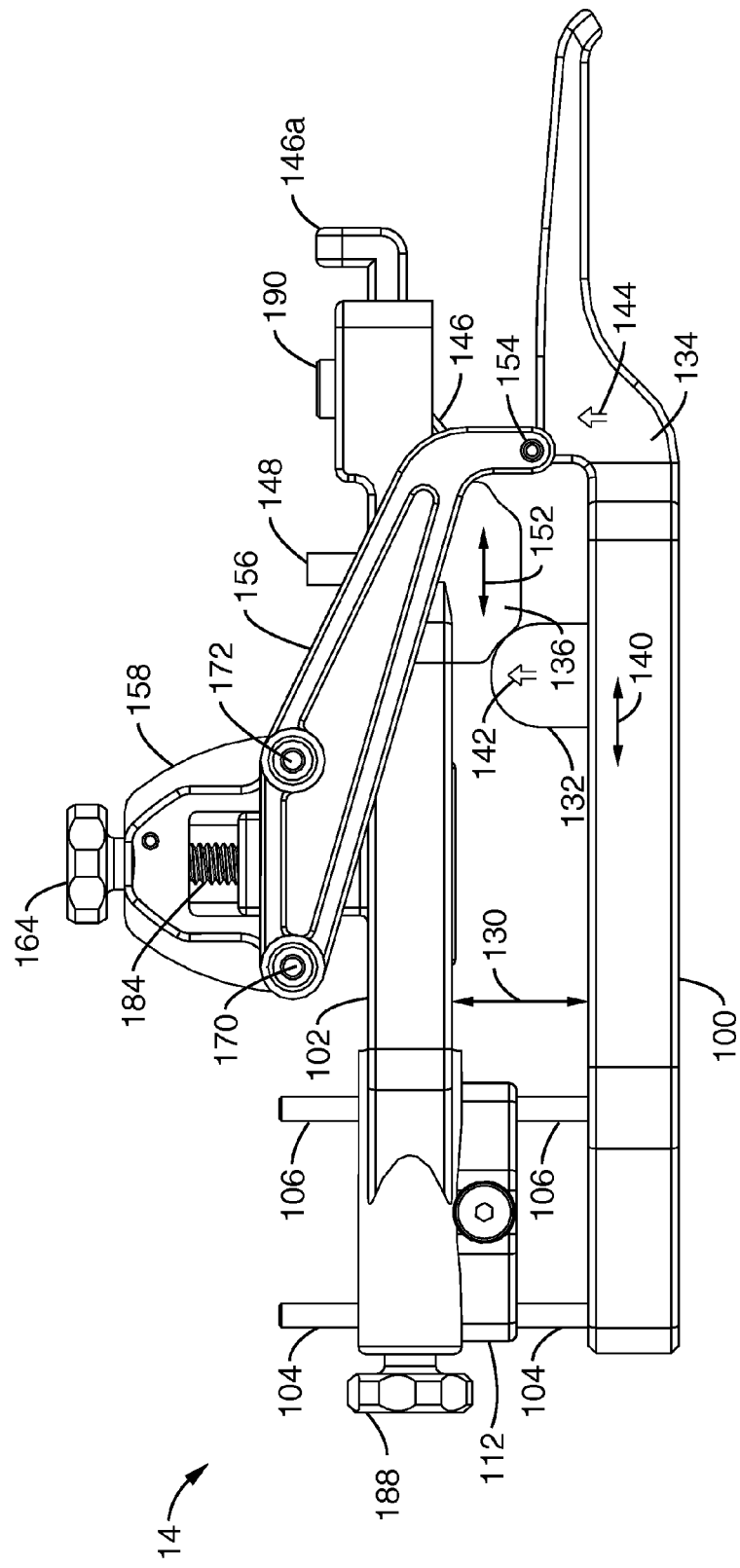
FIG. 5 is a side view of a pin placement guide device according to the present invention.
Figure 6:
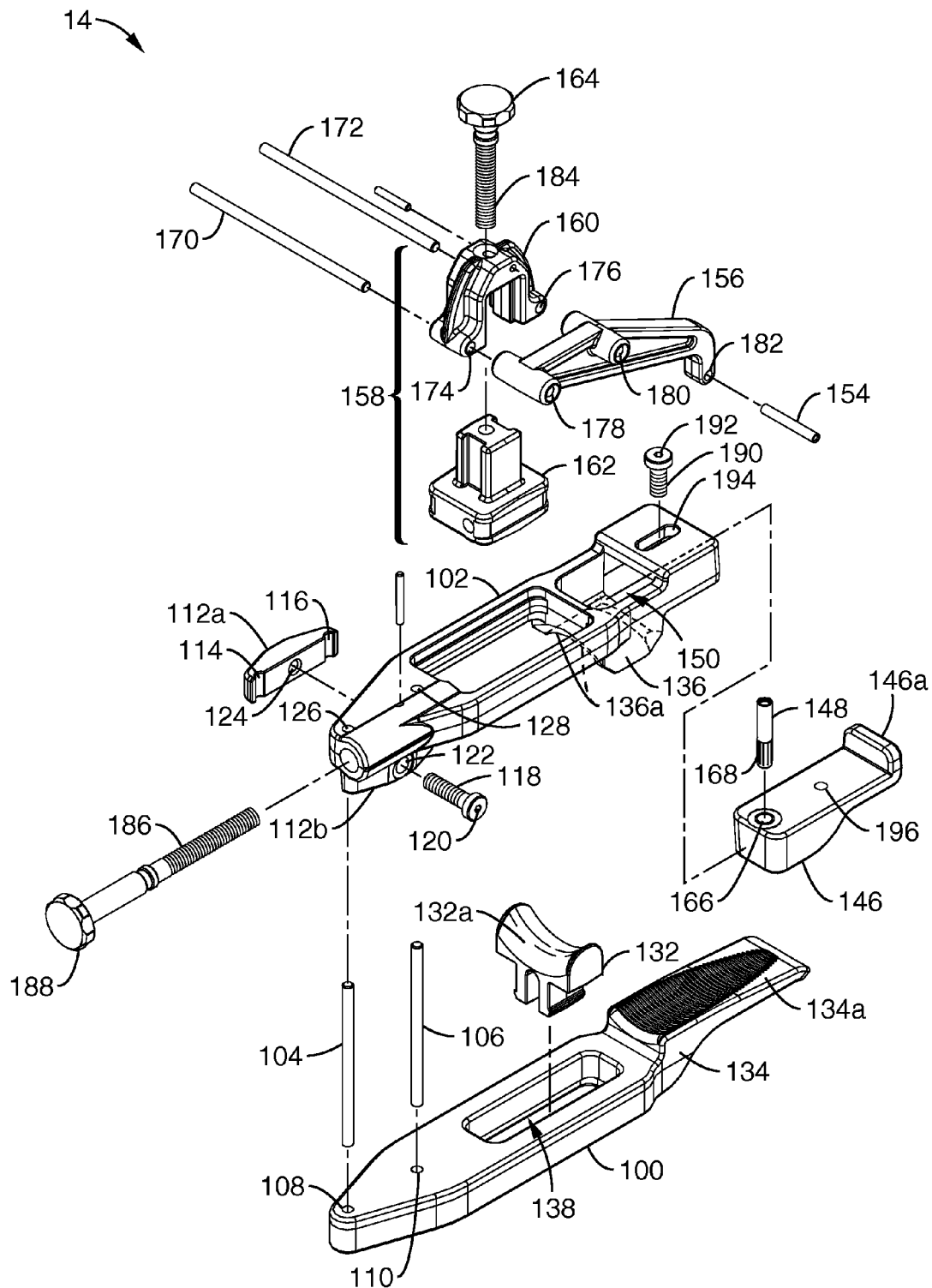
FIG. 6 is an exploded perspective view of the device shown in FIG. 5.

Referring now to FIG. 5 and FIG. 6, an exemplary embodiment of the pin placement guide 14 is illustrated. This component is specifically designed to prepare the finger for insertion of the dorsal 20 and transverse 24 skeletal fixation pins at the proper locations and for the insertion of the pins themselves. Pin placement guide 14 includes a lower beam 100 and an upper beam 102. Each beam can be an integrated element as shown, but could alternatively comprise a set of substantially parallel rails to which the components are coupled. Lower beam 100 is configured to be palmer to the finger when in use and upper beam 102 is configured to be dorsal to the finger when in use. Accordingly, lower beam 100 and upper beam 102 are also referred to herein as "palmar beam" and "dorsal beam", respectively.

The two beams are coupled to each other in a substantially parallel orientation by vertical rails 104, 106 extending in the palmar-dorsal direction from apertures 108, 110 in palmar beam 100 to a clamp 112 on dorsal beam 102. In the embodiment shown, clamp 112 comprises a moveable member 112a and an opposing fixed clamp member 112b which is attached to dorsal beam 102. Moveable member 112a includes a pair of slots 114, 116 which are adapted to receive rails 104, 106. A corresponding pair of opposing slots (not shown) is also provided in clamp member 112b. A threaded lock screw 118, having a hex socket 120, extends through an aperture 122 in clamp member 112b and into a threaded receptacle 124 in clamp member 112a, and is used to lock the position of dorsal beam 102 in relation to palmar beam 100. Note that rails 104, 106 extend into, but not through, palmar beam 100 whereas the rails extend through apertures 126, 128 in dorsal beam 102 to allow for adjustment of the palmar-dorsal distance 130 between palmar beam 100 and dorsal beam 102 (i.e., the height of the dorsal beam above the palmar beam) and can be adjusted to accommodate fingers of different sizes.

While the beam construction thus described is preferred, each beam or both can be replaced with a set of parallel rails that allow for mounting of the components and repositioning thereof as necessary. Further alternative constructions will be readily apparent, such as the use of a single dorsal rail and a single palmar rail rather than two of each, provided that the single rails are constructed in a manner that will permit mounting and sliding of the components without rotation. Beams or rails of non-circular cross section, such as square, rectangular, or elliptical, for example, will serve this purpose. Other examples will be readily apparent to those skilled in the art.

Immobilization of the finger by the pin placement guide 14 is achieved by three blocks: distal palmar block 132, proximal palmar block 134, and dorsal block 136. Distal palmar block 132 is a component that is slidaby coupled to palmar beam 100, proximal palmar block 134 is integrated into palmar beam 100 but could alternatively be a separate component coupled to palmar beam 100, and dorsal block 136 is integrated into dorsal beam 102 but could alternatively be a separate component coupled to dorsal beam 102. When the pin placement guide 14 is properly installed, the distal palmar block 132 will be positioned directly below the distal interphalangeal (DIP) joint and the proximal palmar block 134 will be positioned to extend from a location directly below the proximal interphalangeal (PIP) joint, which is the joint to be treated, back in the proximal direction to support the entire proximal phalanx. The spacing between blocks 132, 134 is made variable by slidably coupling the distal palmar block 132 to palmar beam 100 in a slot 138 for movement in the longitudinal direction as indicated by the arrow 140. Arrows 142, 144 can be printed on blocks 132, 134, respectively, to enable the surgeon to position the blocks correctly, with the distal arrow 142 pointing directly to the crease at the DIP joint and the proximal arrow 144 pointing directly to the crease in the patient's finger at the PIP. A dorsal drill guide block 146, which includes a finger tab 146a at its end to facilitate movement, controls the position of a dorsal drill (and pin) guide tube 148 and is slidably coupled to dorsal beam 102 in a slot 150 so as to permit its position along the dorsal beam to be adjusted in the longitudinal direction as indicated by the arrow 152. In use, the dorsal block 136 will be positioned between the two palmar blocks 132, 134, directly above the middle phalanx at approximately the midpoint of the middle phalanx. A hollow transverse pin guide tube 154 is included on a movable transverse pin guide 156 which in turn is coupled to the upper portion of a height adjustment block 158 formed in upper and lower parts 160, 162, respectively, and whose height is controlled by a knob 164.

The palmar-facing surfaces 132a, 134a of the distal palmar block 132 and the proximal palmar block 134, respectively, contact the palmar side of the finger and are finger-contoured, as this term is defined above. The dorsal-facing surface 136a of the dorsal block 136 is likewise finger-contoured. As illustrated, palmar-facing surface 134a is optionally grooved or similarly treated to prevent finger slip, as could any of the surfaces that make contact with the skin. Dorsal drill guide tube 148 comprises a hollow tube that passes through an aperture 166 in the dorsal drill guide block 146 and forms a channel that serves as a guide for the drill bit that will be used to drill a hole in the middle phalanx and as a guide for the dorsal pin that will be inserted in the hole. Threads or ridges 168 in dorsal drill guide tube 148 provide for secure retention thereof in aperture 166. Note that the channel formed by dorsal drill guide tube 148 also passes through dorsal block 136.

The movable transverse pin guide 156 retains transverse pin guide tube 154 such that, when mounted to the remainder of the pin placement guide 14 and properly positioned, the transverse pin guide tube will be at one side of the finger and aligned with the axis of the PIP joint. The channel within the transverse pin guide tube 154 is transverse both to the channel in the dorsal drill guide tube 148 and to the palmar beam 100 and dorsal beam 102. The transverse pin guide tube 154 serves as a guide for the self-drilling transverse pin that will be inserted in the axis of the PIP joint.

Transverse pin guide 156 is coupled to the upper portion 160 of the height adjustment block on the dorsal beam by way of transverse rails or posts 170, 172 which extend through apertures 174, 176, respectively, in the upper portion 160 of the height adjustment block and through corresponding apertures 178, 180 on the carrier that fit over the rails 170, 172, respectively. Transverse pin guide tube 154 extends through an aperture 182 in the transverse pin guide 156.

The two rails 170, 172 can be replaced by a single rail of non-circular cross section or by more than two rails, in either case with a corresponding variation in the configuration of the sleeves 178, 180. Since the transverse rails 170, 172 extend from both sides of the height adjustment block 158, the transverse pin guide 156 can be mounted to either side of the block, offering the surgeon the choice of drilling the PIP joint and mounting the transverse pin from either the radial side of the finger or the ulnar side of the finger. Positioning of the transverse pin guide tube 154 is achieved in the palmar-dorsal (vertical) direction by a height adjustment of the height adjustment block 158 relative to the dorsal beam 102 by turning the knob 164 which causes rotation of a threaded shaft 184. Positioning of the transverse pin guide tube 154 in the proximal-distal (longitudinal or horizontal) direction is achieved by a horizontal (longitudinal) threaded shaft 186 that controls the longitudinal position of the height adjustment block 158 and the transverse pin guide 156. The threaded shaft is turned manually by an end knob 188. The transverse rails 170, 172 are affixed to the upper half 160 of the block, while the lower half 162 of the block is coupled to the dorsal beam 102.

As discussed above, dorsal drill guide block 146 includes a finger tab 146a to facilitate movement of the block in relation to dorsal beam 102 and provide for proper positioning of dorsal drill guide tube 148. A threaded lock screw 190, having a hexagonal socket 192, extends through an elongated slot 194 in dorsal beam 102 and into a threaded receptacle 196 in dorsal drill guide block 146 to prevent further movement when dorsal drill guide block 146 is properly positioned.

Figure 8:
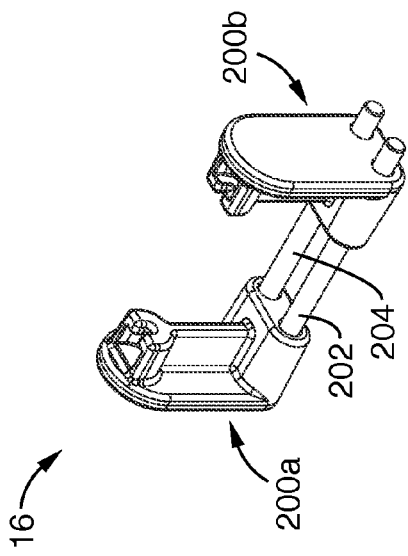
FIG. 8 is an assembled perspective view of the device shown in FIG. 7 with the blocks spread apart.
Figure 9:
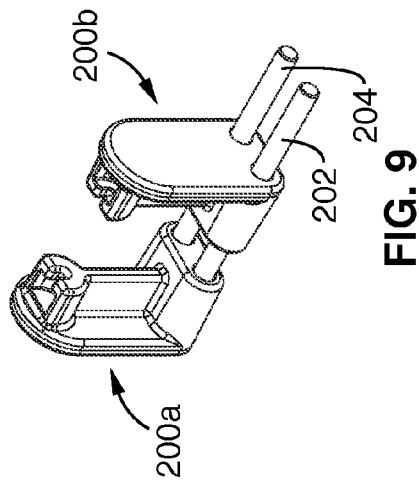
FIG. 9 is an assembled perspective view of the device shown in FIG. 7 with the blocks compressed together, thus illustrating the adjustability of the device in relation to FIG. 8.
Figure 7:
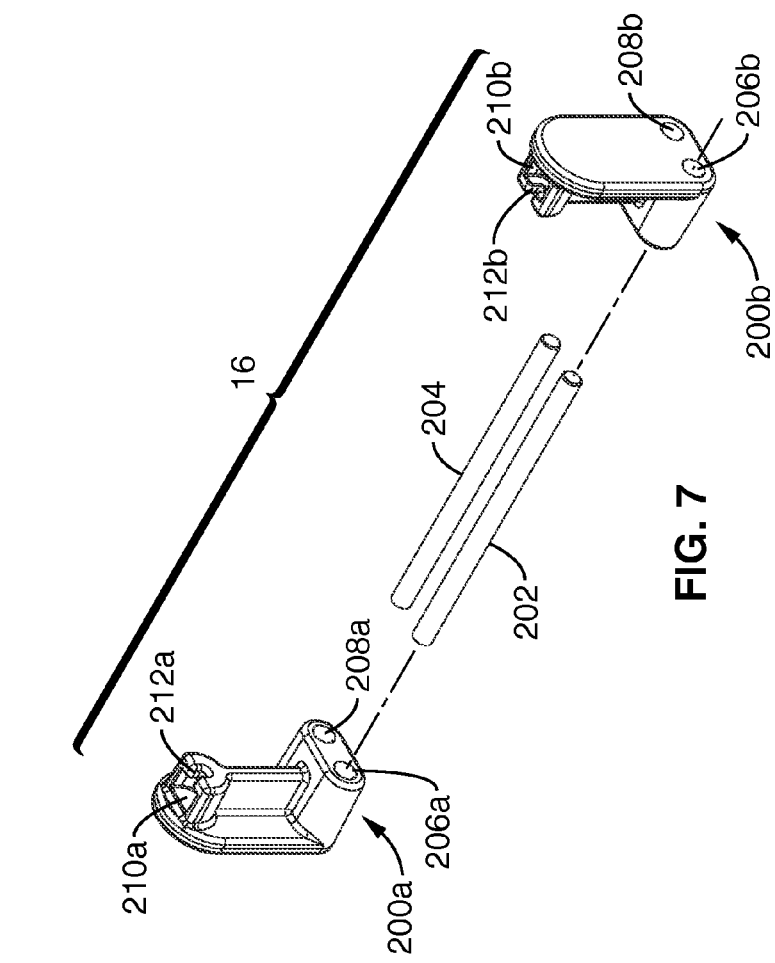
FIG. 7 is an exploded perspective view a cap application device according to the present invention.

Referring now to FIG. 7 through FIG. 9, an exemplary embodiment of the cap applicator 16 is illustrated. In the embodiment illustrated, cap applicator 16 comprises a pair of opposing blocks 200a, 200b which are supported by a pair of rails 202, 204 which fit into apertures 206a, 208a and 206b, 208b, in blocks 200a, 200b, respectively. The apertures extend completely through at least one of the blocks, shown here as extending through block 200b, so that the at least one block is slidably coupled to the rails and can be repositioned toward or away from the opposing block as illustrated in FIG. 8 and FIG. 9. Alternative rail configurations will be readily apparent, such as the use of a single rail constructed in a manner that will permit mounting and sliding of the components without rotation. Rails of non-circular cross section, such as square, rectangular, or elliptical, for example, will serve this purpose.

Blocks 200a, 200b include receptacles 210a, 210b, respectively, for receiving caps 26a, 26b, respectively, as well as receptacles 212a, 212b, respectively, for receiving transverse pin 24. After inserting the caps and transverse pin into these receptacles, the blocks can be drawn together to press the caps onto the transverse pin.

Referring again to FIG. 1, pin spacer 18 includes a first end 250 with a slot 252 for receiving dorsal pin 20 and a second end 254 with an aperture 256 for receiving transverse pin 24. First end 250 is configured for determining the final length of dorsal pin 20, and second end 254 is configured for determining the final length of the portion of transverse pin 24 on each side of the finger. It will be readily apparent that other slot/ aperture configurations (e.g., two slots, two apertures, reversing the slot and aperture shown) could be employed as well.

An embodiment of a method for using surgical kit 10 and its various components is illustrated with reference to the foregoing figures as well as FIG. 10 through FIG. 34. In the following discussion, a fractured finger 300 will be treated. Shown associated with finger 300 is a proximal phalanx 302, a PIP joint 304, a middle phalanx 306, a DIP joint 308, and a distal phalanx 310.

Figure 10:
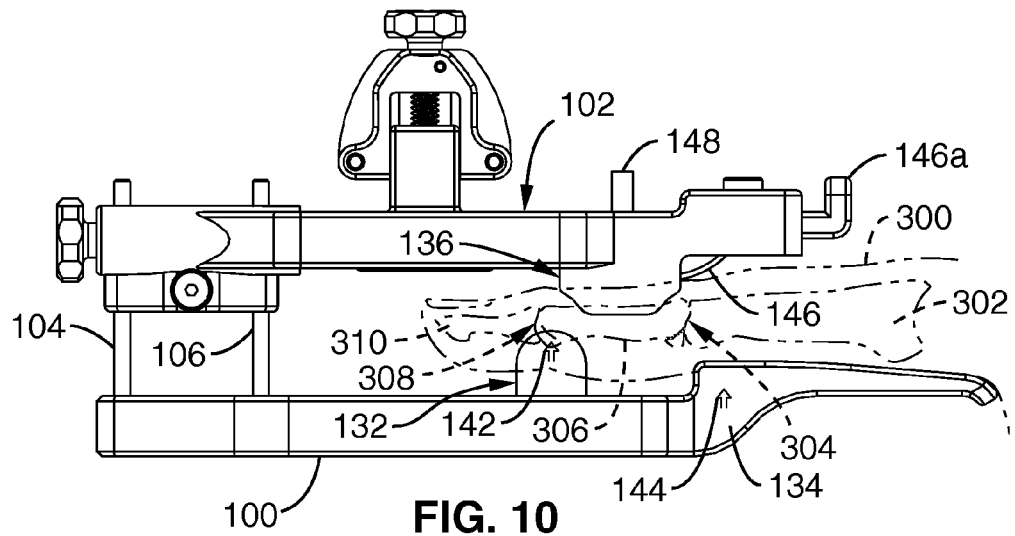
FIG. 10 through FIG. 36 are diagrams illustrating an embodiment of a method for treating a PIP joint fracture in the index finger of a subject according to the present invention using the surgical kit shown in FIG. 1.

Referring to FIG. 5, FIG. 6 and FIG. 10, pin placement guide 14 is made ready for reduction of the finger. As illustrated in FIG. 10, this is accomplished by first removing transverse pin guide 156 from rails 170, 172. Palmar beam 100 and dorsal beam 102 are then spread apart along rails 104 and 106 to facilitate insertion of the finger into the pin placement guide. The fractured finger 300 is placed onto palmar beam 100 with the palm of the hand substantially parallel to palmar beam 100 (the fingernail should not be aligned with the palmar beam by rotating the finger on the beam). The finger is then positioned with the PIP flexion crease aligned with the proximal arrow 144 on palmar beam 100 and distal palmar block 132 is moved in slot 138 until the distal arrow 142 is aligned with the DIP flexion crease.

Figure 11:
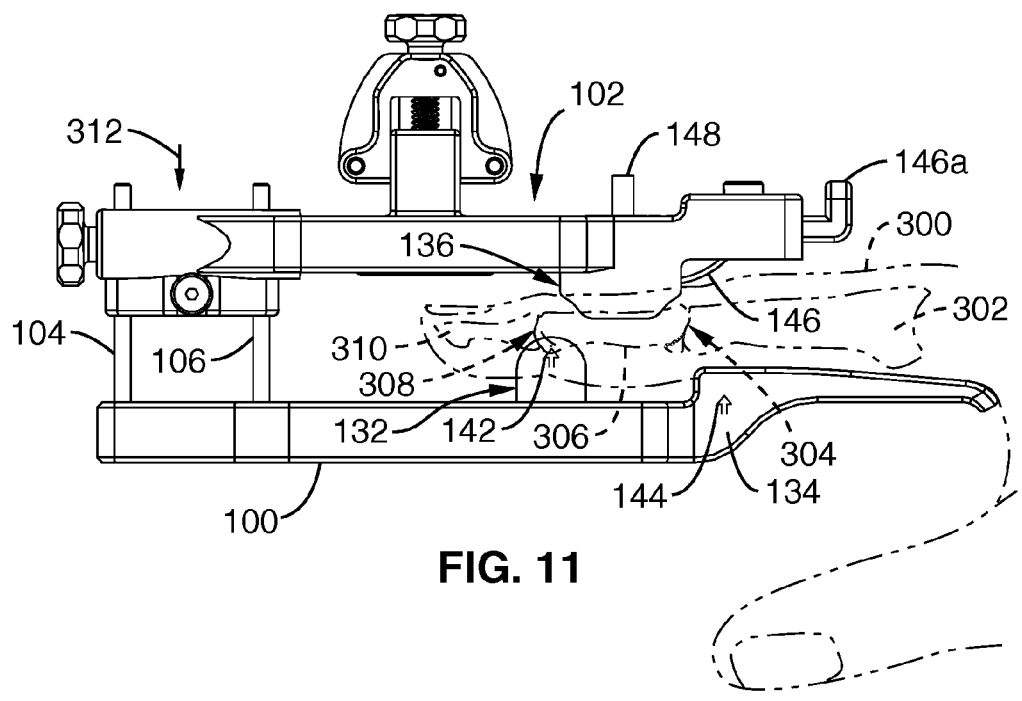

Referring to FIG. 11, manual traction is applied to the PIP joint 304 as the finger is gently clamped into the pin placement guide. The subluxed joint is reduced by applying force indicated by arrow 312 to lower the dorsal beam 102 onto the finger. The fracture is reduced when joint congruency is restored. Three point fixation created by the two palmar blocks 132, 134 and the dorsal block 136 maintain joint reduction during pin installation. Fluoroscopy can be used to confirm joint reduction.

Figure 12:
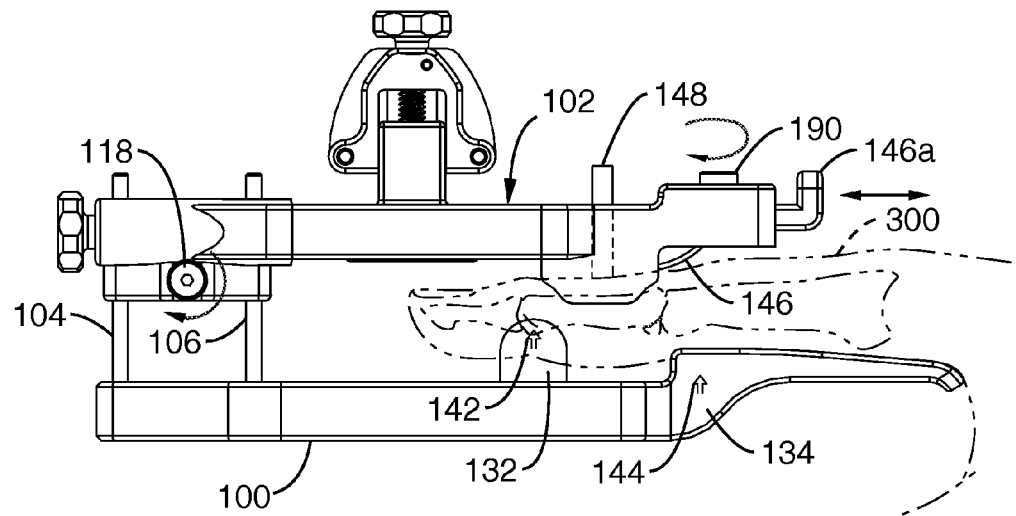

As illustrated in FIG. 12, the dorsal beam 102 is then locked in position relative to palmar beam 100 by rotating the distal lock screw 118 with hex wrench 28. Using finger tab 146a, dorsal drill guide block 146 is adjusted to ensure that the dorsal drill guide tube 148 is positioned distal to the fracture and slightly proximal to the mid-shaft of the middle phalanx. Proper position of the dorsal drill guide can be confirmed using fluoroscopy. The dorsal drill guide is then locked in position by rotating dorsal lock screw 190 with hex wrench 28.

Figure 13:
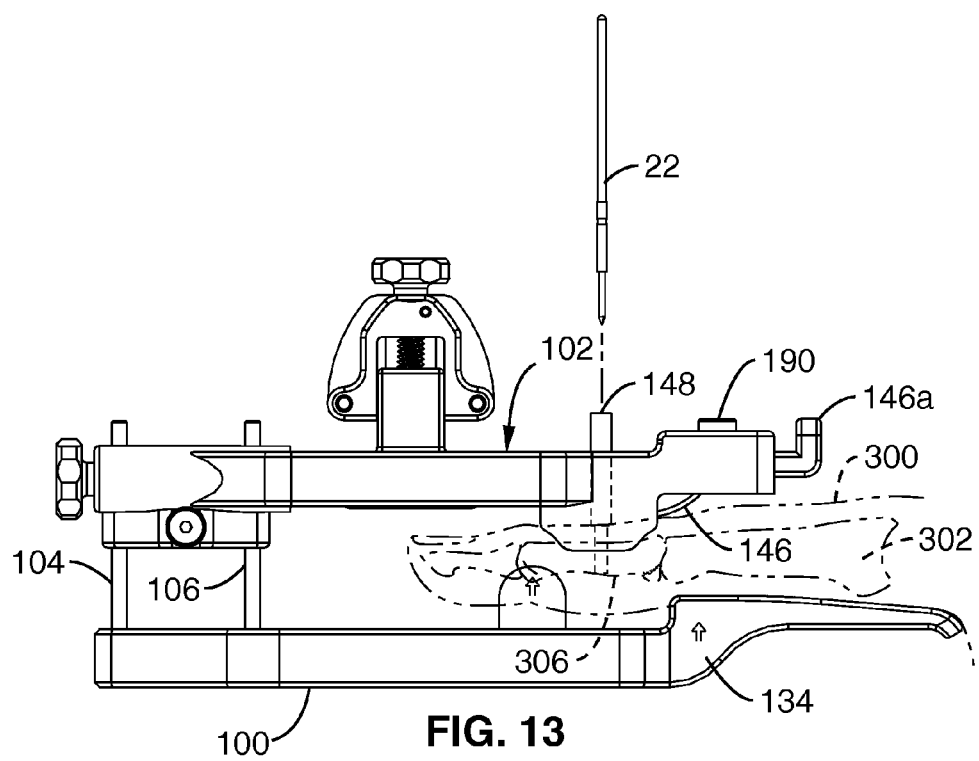

Next, referring to FIG. 13, pre-drill bit 22 is inserted into dorsal drill guide tube 148 and used to drill through both cortices of the middle phalanx 306. The pre-drill bit should extend through, but not beyond, the palmar cortex. Keeping the drill guide tube 148 aligned with the pre-drilled hole, the pre-drill bit 22 is then removed from the bone. Note that alignment of drill guide tube 148 and the pre-drilled hole should be maintained until the dorsal pin 20 is inserted.

Figure 14:
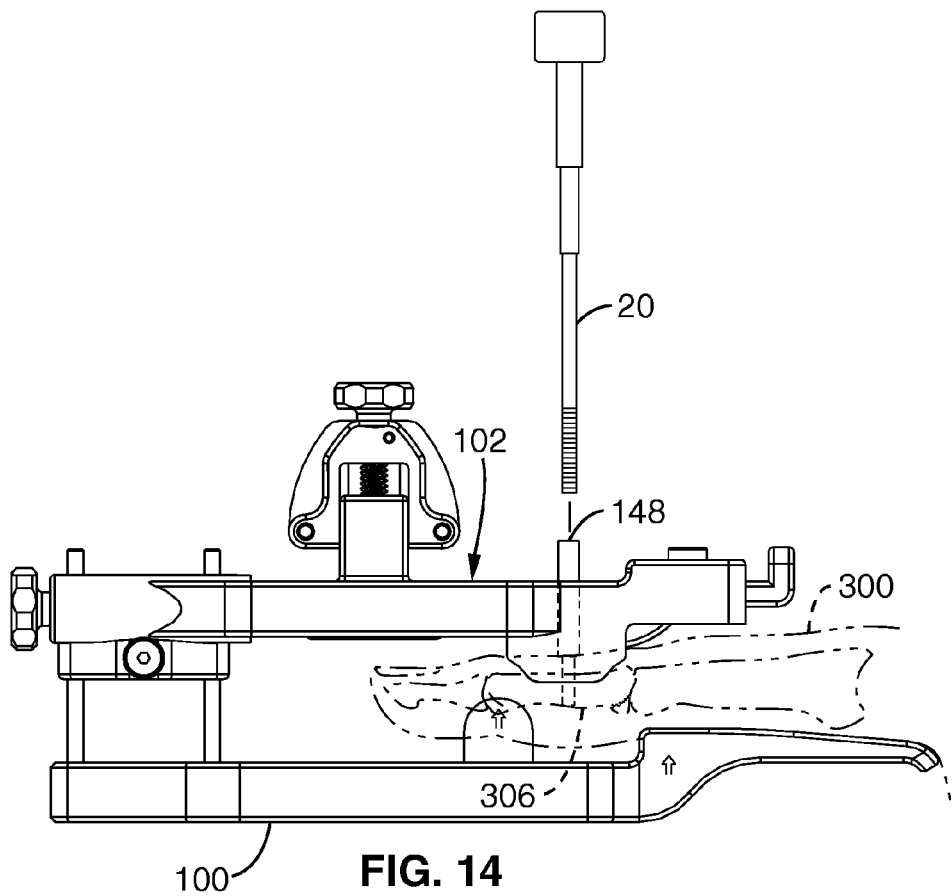
Figure 15:
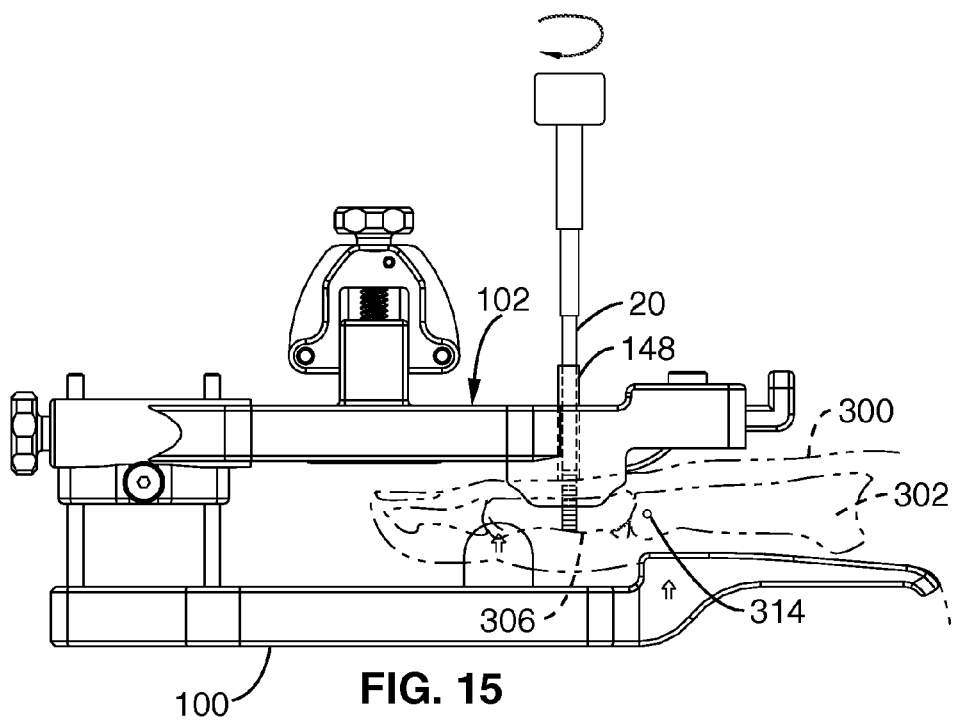
Figure 16:
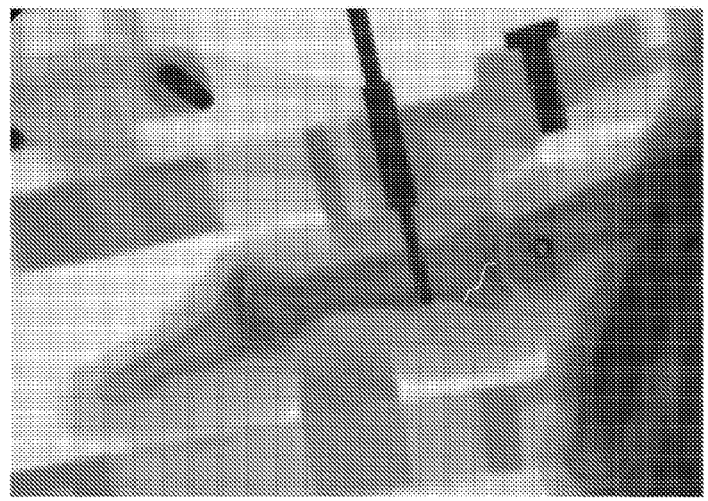

Referring to FIGS. 14 and 15, the dorsal pin 20 is then manually threaded into the middle phalanx 306 by rotating it clockwise into the pre-drilled bone. The depth of insertion should stop short of the flexor tendons. Referring also to FIG. 16, pin depth can be confirmed by advancing the dorsal pin 20 in the pre-drilled hole using fluoroscopic control until the pin's tip is flush with the palmar cortex of the bone.

Figure 17:
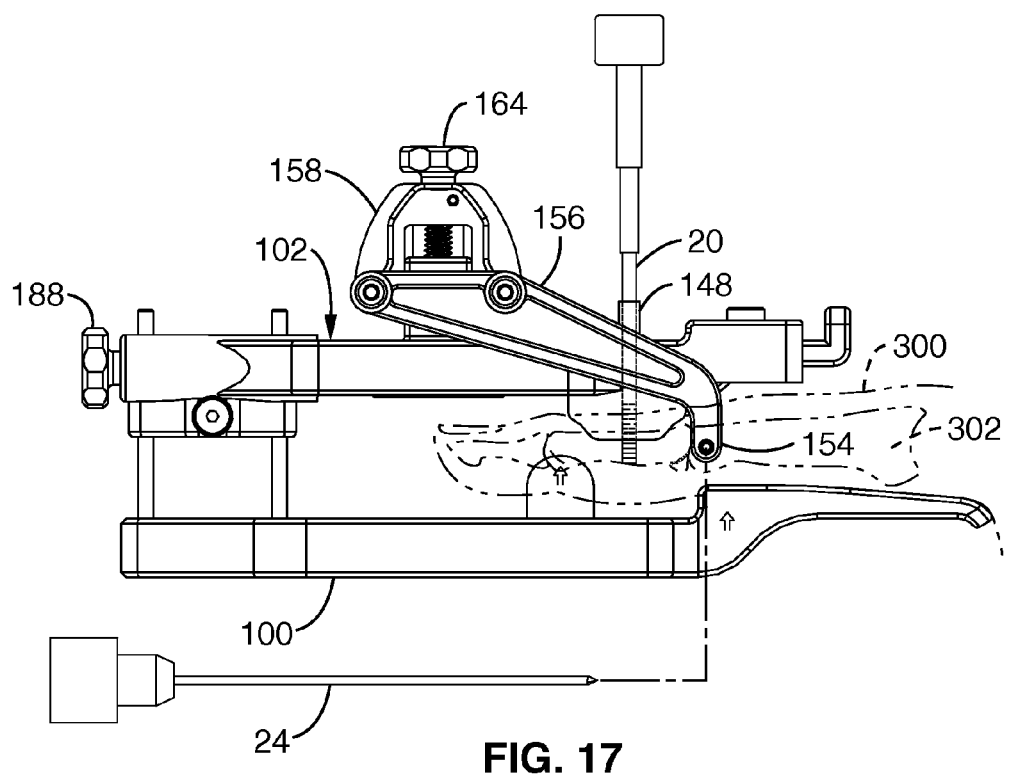
Figure 18:
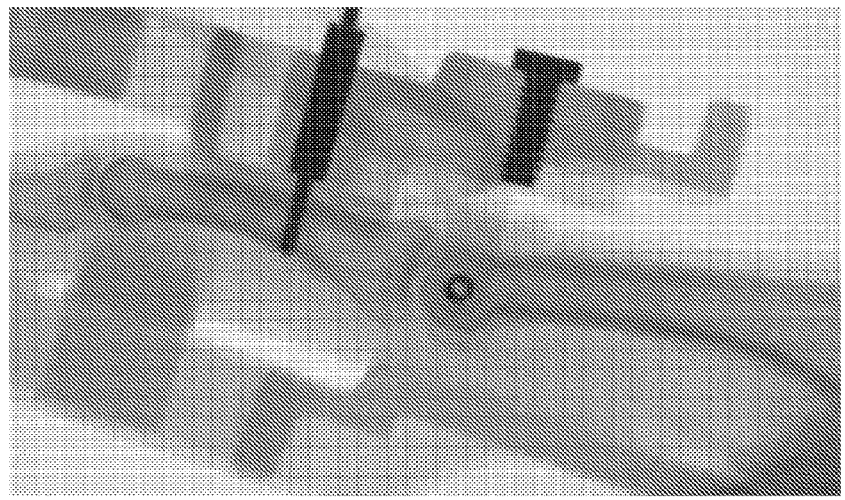

Next, the transverse pin 24 is inserted. Referring to FIG. 15 and FIG. 17, this is accomplished by installing the transverse pin guide 156 onto the side (radial or ulnar) of the height adjustment block 158 of pin placement guide 14 that is technically easiest for pin insertion. The distal/proximal 188 and dorsal/palmar 164 adjustment screws are used with fluoroscopic control to align the metal drill guide tube 154 with the center 314 (see FIG. 15) of the head of the proximal phalanx 302. The drill guide tube 154 is then positioned snug against the skin before obtaining a final lateral fluoroscopic view centered on the tube axis to confirm the optimal position for the transverse pin 24. As illustrated in FIG. 18, when the transverse pin guide tube 154 is properly aligned over the head of the proximal phalanx 302, the end of the tube will appear concentric with the head of the proximal phalanx. Next, using a power drill, the transverse pin 24 is inserted through the head of the proximal phalanx 302 until approximately 1 cm of the pin extends out of the skin on the far side. The transverse pin will be trimmed to the final length after removal of the pin placement guide.

In some treatment protocols, instead of positioning the transverse pin 24 concentric with the head of the proximal phalanx as described above, it may be desirable to position the pin guide tube slightly dorsal and/or proximal of the axis of rotation of the joint. This would be the case, for example, where the concentric positioning could result in the collateral ligament being pinned to the bone by transverse pin 24.

Figure 19:
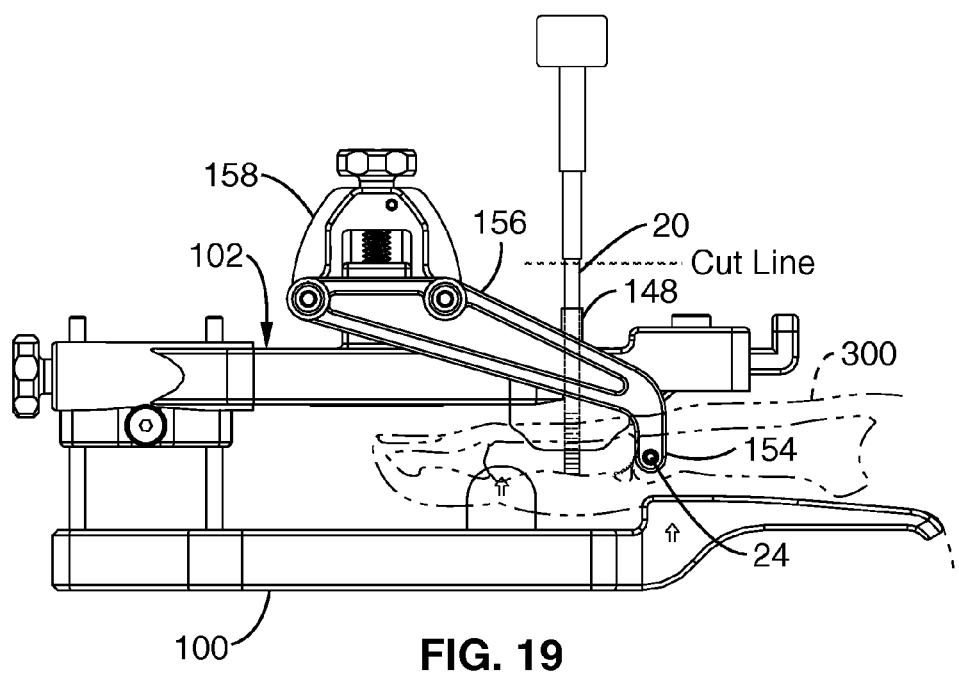

Referring to FIG. 19, the dorsal pin 20 is then cut just below its shoulder to allow for removal of pin placement guide 14.

Figure 20:
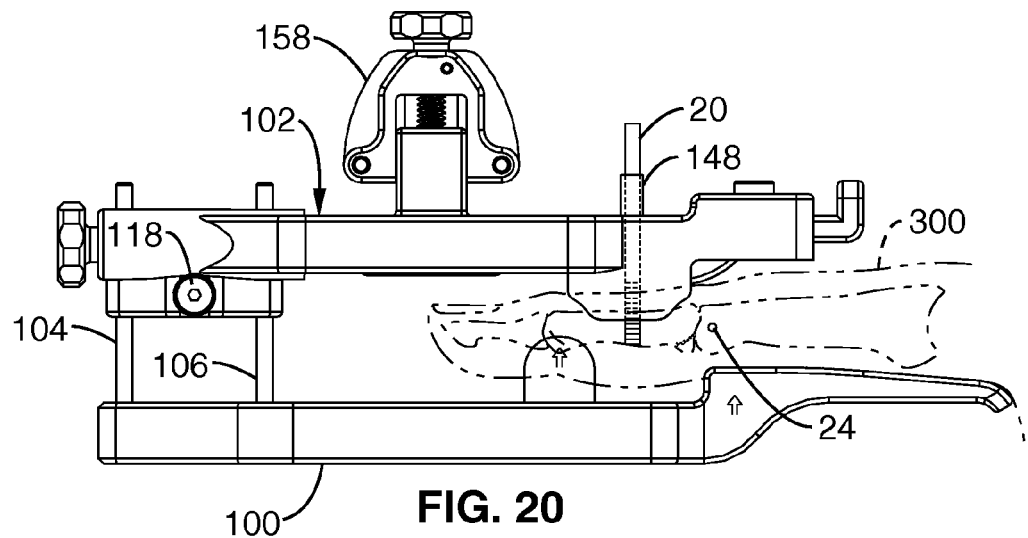
Figure 21:
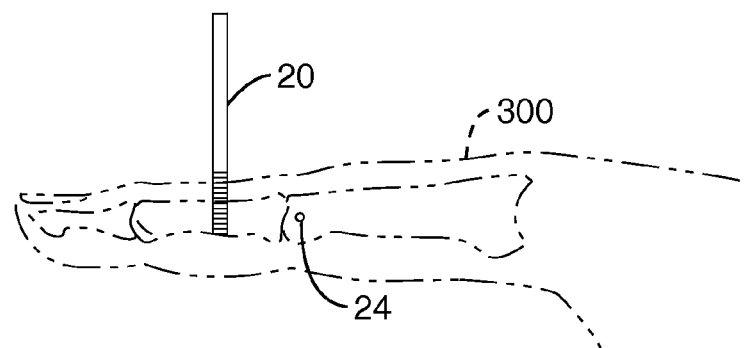

The dorsal pin will be trimmed to final length after removal of the pin placement guide. The transverse pin guide 156 is then removed from height adjustment block 158 as FIG. 20 illustrates. Next, the distal lock screw 118 is loosened so that dorsal block 102 can be removed from rails 104, 106 and palmar beam 100. Note that the transverse pin guide tube 154 slides over the unobstructed length of transverse pin 24 when transverse pin guide 156 is removed, and that the dorsal drill guide tube 148 slides over the unobstructed length of dorsal pin 20 when dorsal beam 102 is removed. FIG. 21 illustrates the finger after pin placement guide 14 has been removed.

Figure 22:
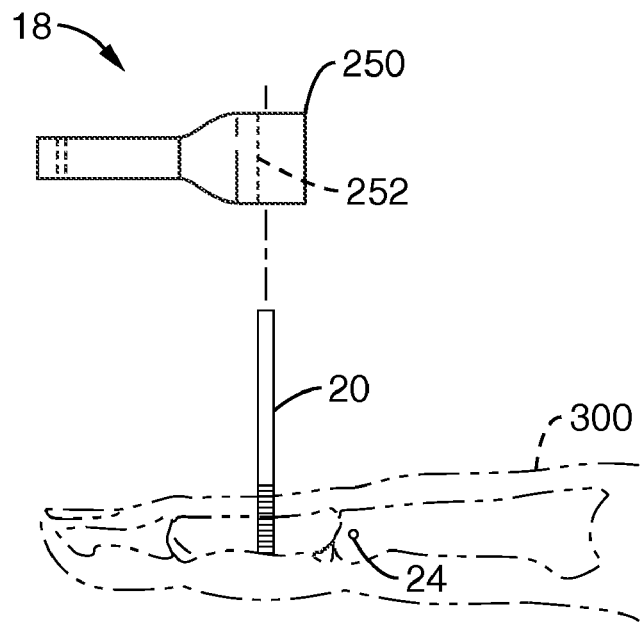
Figure 23:
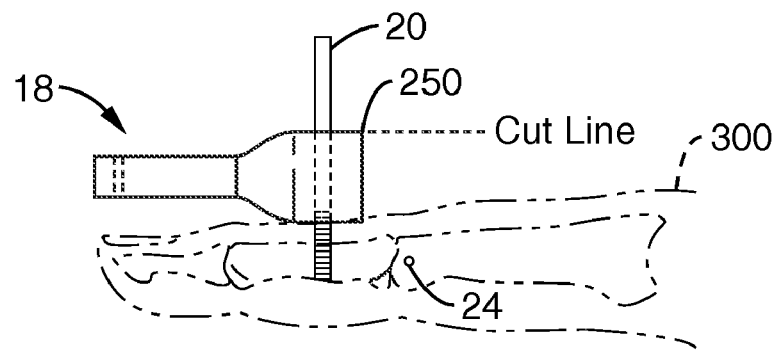
Figure 24:
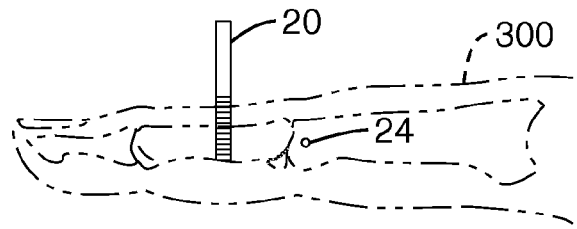
Figure 25:
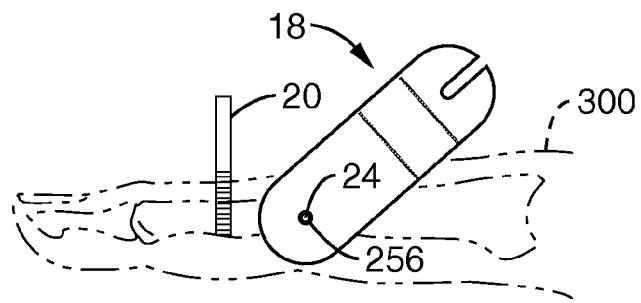
Figure 26:
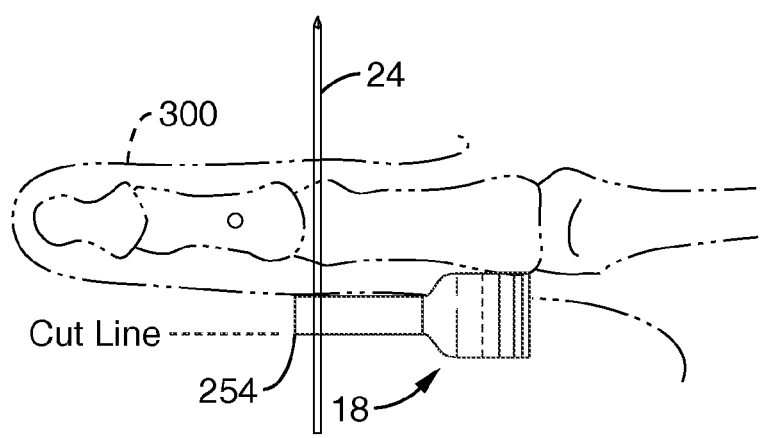

The dorsal 20 and transverse 24 pins can now be trimmed to proper length using pin spacer 18. Referring also to FIG. 1, and as illustrated in FIG. 22 through FIG. 23, dorsal pin 20 is trimmed by placing the slot 252 in the dorsal pin end 250 of pin spacer 18 over the dorsal pin 20 and against the dorsal skin of the patient's finger. The dorsal pin 20 is then cut off at the top of the pin spacer 18 as illustrated by the cut line in FIG. 23. As illustrated in FIG. 25 and FIG. 26, the transverse pin is trimmed by sliding aperture 256 in the transverse pin end 254 of pin spacing 18 over the transverse pin 24 and against the skin on the side of the patient's finger. Transverse pin 24 is then cut off at the side of the pin spacer 18 as illustrated by the cut line in FIG. 26. This procedure is applied to the portion of the transverse pin that extends outward from each side of the patient's finger.

Figure 27:
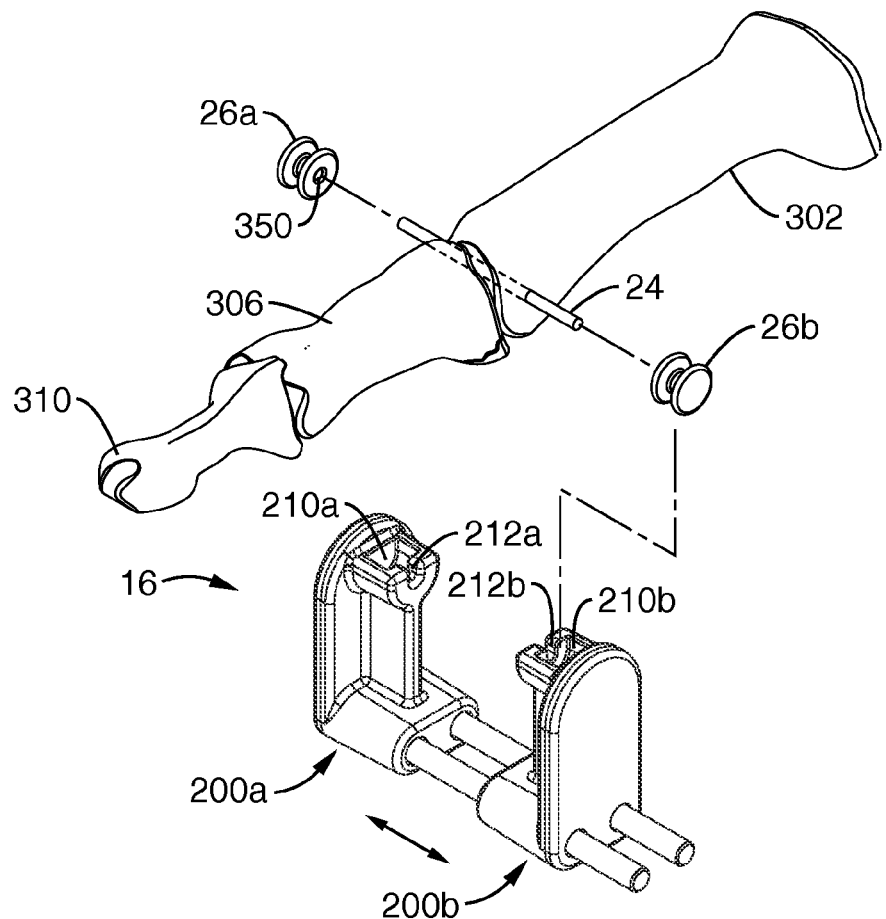
Figure 28:
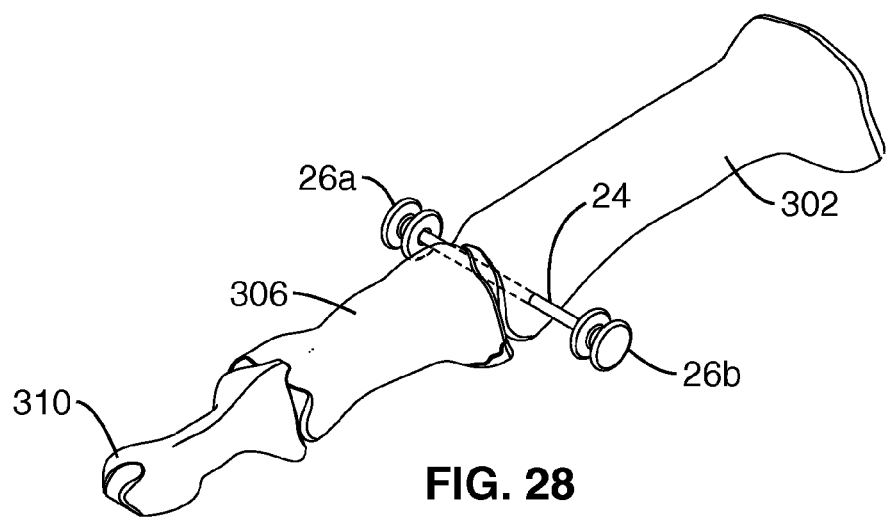
Figure 29:
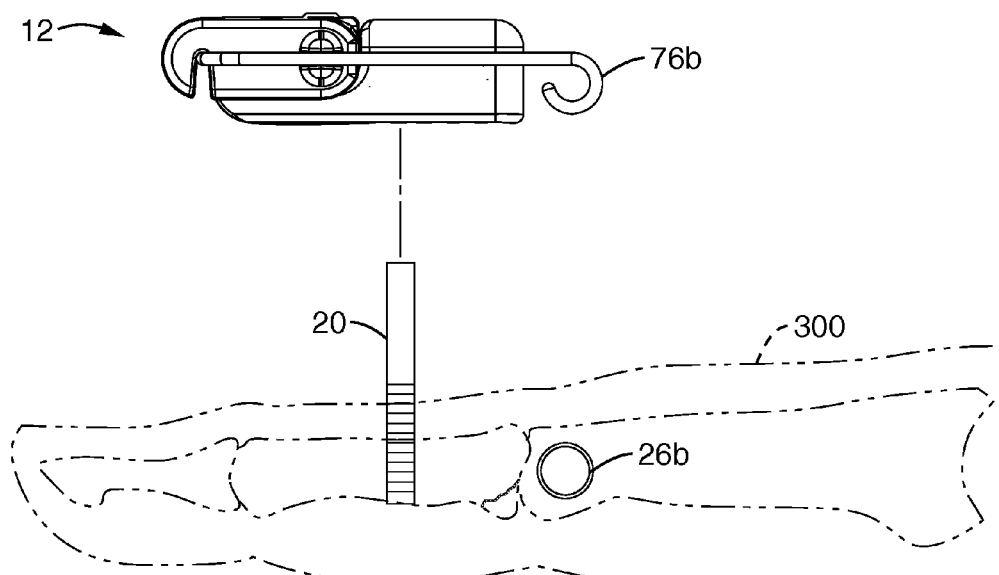

Referring now to FIGS. 27 and 28, pin caps 26a, 26b are then placed into receptacles 210a, 210b of cap applicator 16, respectively. Holes 350 are provided in each of pin caps 26a, 26b to receive transverse pin 24. The slots 212a, 212b are then aligned with both ends of the transverse pin 24 and the blocks 200a, 200b are squeezed together until the pin caps are firmly seated on the ends of the transverse pin. This clamps the transverse pin 24 between the pin caps 26a, 26b.

Figure 30:
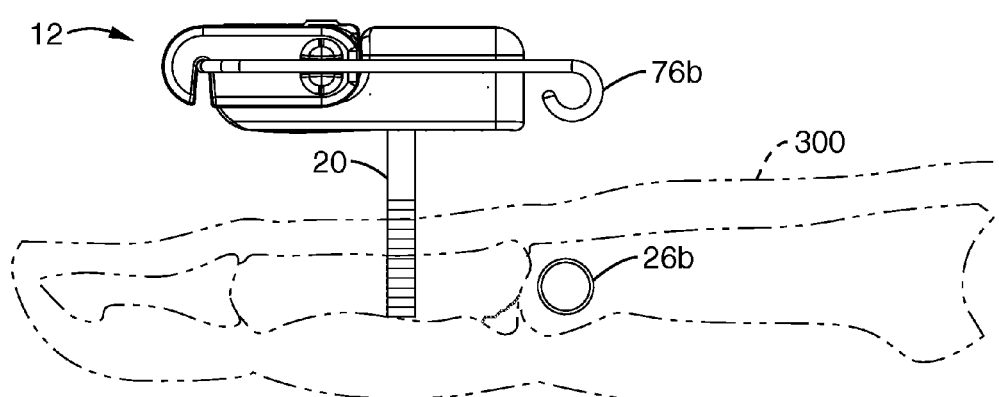
Figures 31, 32:
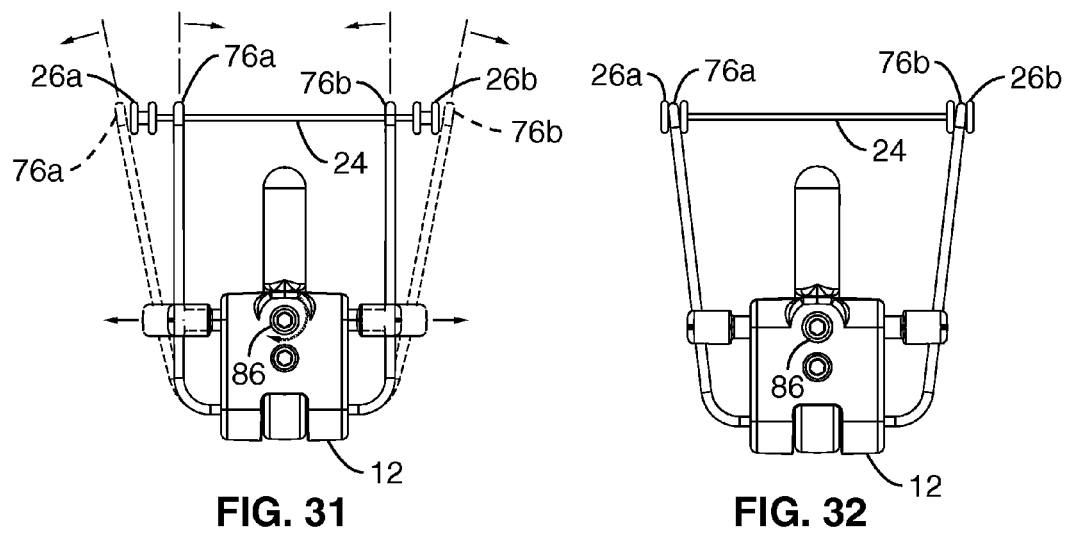

The dorsal and transverse pins are now ready for installation of the F3 device 12. Referring to FIG. 2 through FIG. 4 and FIG. 29, the dorsal pin 20 is placed into one of the holes 96 in the underside of the F3 device. The particular hole chosen should be one that positions the hooks 74a, 74b directly dorsal to the pin caps 26a, 26b, respectively, as illustrated in FIG. 30. Next, referring to FIG. 31, the hex wrench 28 (FIG. 1) is used to rotate the width adjustment screw 86 so the distance between the wire hooks 76a, 76b is the same as that between pin caps 26a, 26b as illustrated in FIG. 32.

Figure 33:
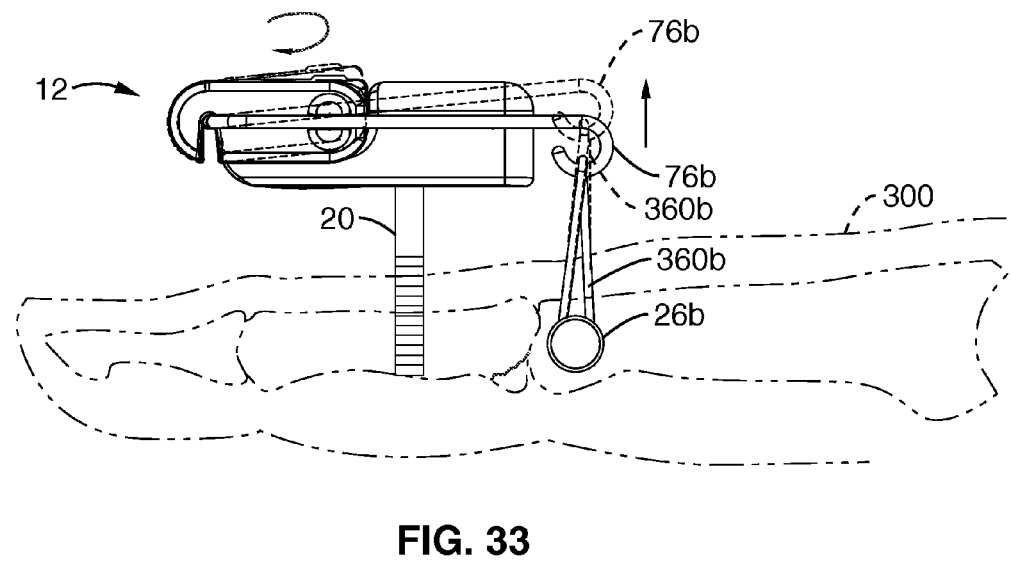

Once wire hooks 76a, 76b are aligned with pin caps 26a, 26b, respectively, an elastic band is installed between each hook and each corresponding pin cap. FIG. 33 illustrates the installation of an elastic band 360b between wire hook 76b and pin cap 26b. Installation of a biasing member such as an elastic band 360a (shown in FIG. 34) between the wire hook 76a and pin cap 26a on the opposite side of the F3 device 12 is the same. Preferably, prior to installation of the elastic bands, it is preferable to rotate tension adjustment screw 66 so that the wire hooks 76a, 76b are lowered to a position that generates the least amount of tension from the bands. The tension adjustment screw is then rotated in the opposite direction to move the hooks upward and apply the desired amount of tension. As discussed previously, tension can also be adjusted by increasing the number of elastic bands or by using elastic bands with different elasticity factors either alone or in combination with the tension adjustment screw.

If the joint has re-subluxed, manual traction may need to be applied as the tension adjustment screw 66 is used to increase the band tension. The increasing band tension will hold the base of the middle phalanx in alignment with the head of the proximal phalanx.

Figure 34:
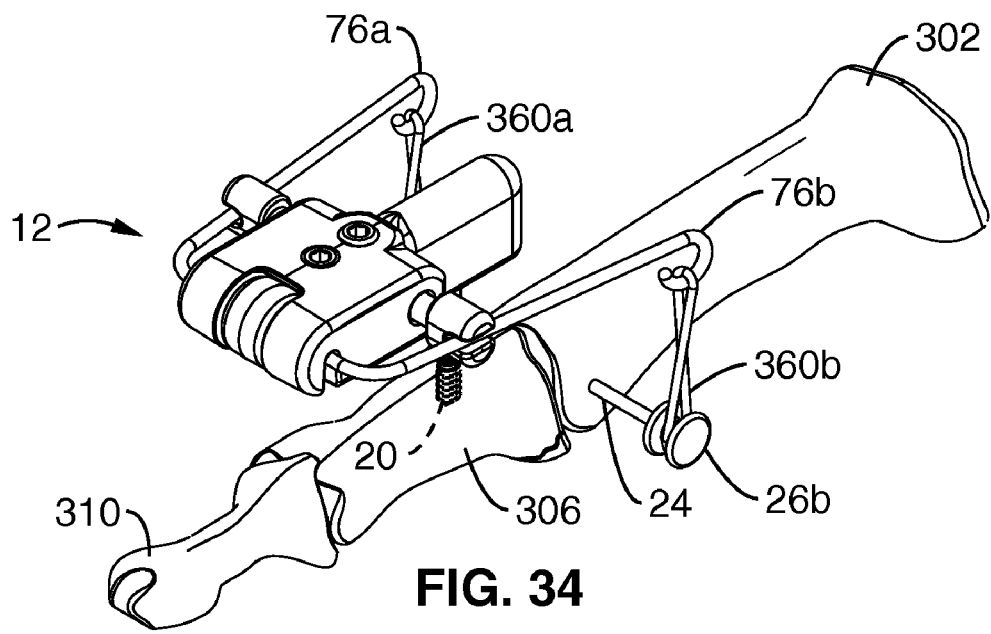
Figure 36:
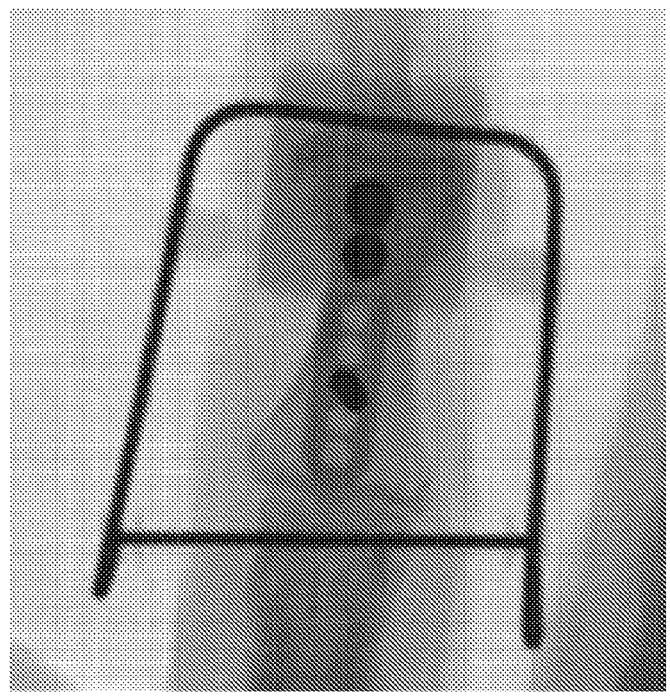
Figure 35:
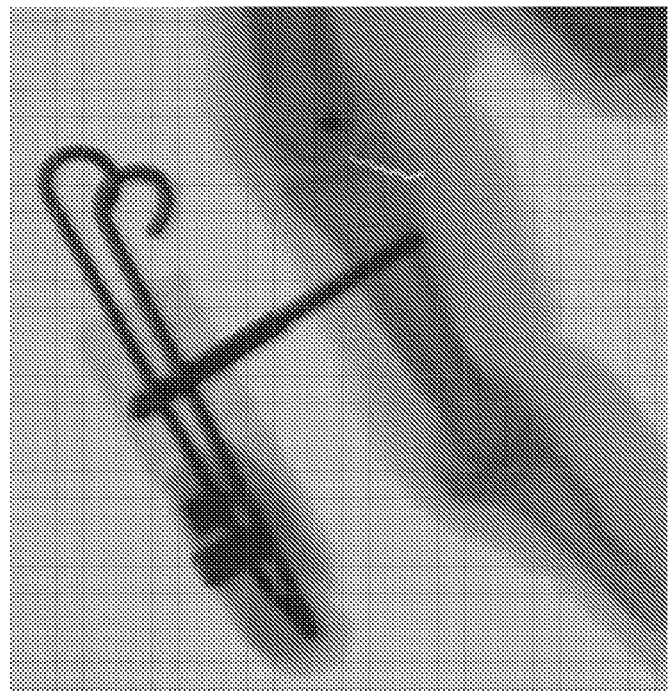

Using fluoroscopy, the next step is to confirm the minimum force generally required to maintain a concentric joint reduction. A reasonably full arc of active and passive PIP joint motion should be available. Lateral fluoroscopic views with the patient actively flexing and extending the finger can be used to judge the ability of the device to maintain concentric joint reduction. FIG. 34 schematically illustrates the finished installation. FIG. 35 is a lateral x-ray depicting the correct installation of the F3 device. As can be seen in this particular treatment protocol, the transverse pin 24 was inserted through the axis of rotation of the PIP joint but it may alternatively be desirable to insert the transverse pin slightly dorsal and/or proximal of the axis of rotation of the joint as previously described. The dorsal pin extends through, but not beyond, the palmar cortex of the middle phalanx. FIG. 36 is an A/P x-ray depicting the correct installation of the F3 device. As can be seen, the transverse pin extends through the head of the proximal phalanx parallel to the articular surface.

It will be appreciated that positioning the drill/pin guide tubes and confirming proper drilling position can be facilitated by fluoroscopic or x-ray imaging. To assist in this imaging, the drill guide tubes can be fabricated from a radiodense material while the adjacent portions of the structures are fabricated from a radiolucent material. Alternatively, the guide tubes can be fabricated from a radiolucent material while the pins themselves are fabricated from a radiodense material. In this alternative, the pins will be held in the guide tubes during positioning of the guide tubes. The dorsal pin would then be removed once positioning is accomplished to allow insertion of the drill bit, whereas the self-drilling transverse pin would remain in position.

Figure 38:
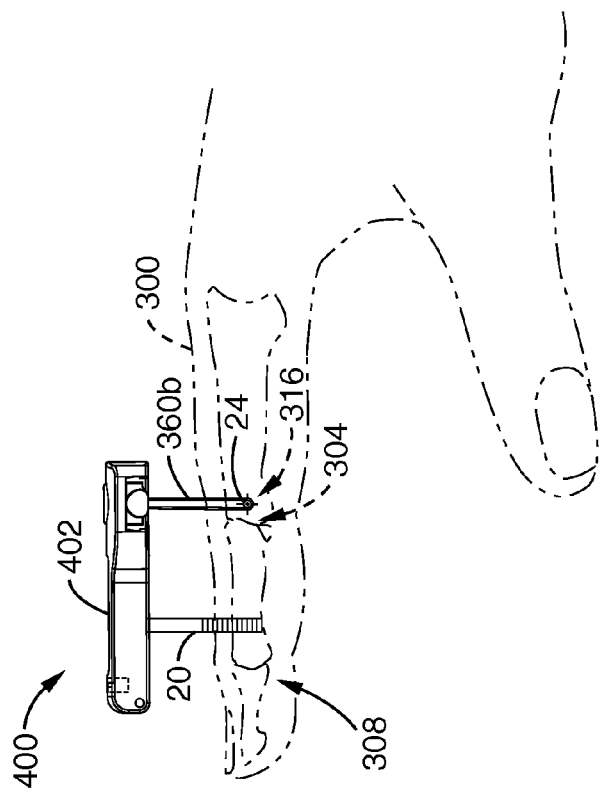
FIG. 38 is a side view of the device shown in FIG. 37, illustrating reduction of the fracture with angle $\alpha$ set to zero and with no flexure of the finger.
Figure 37:
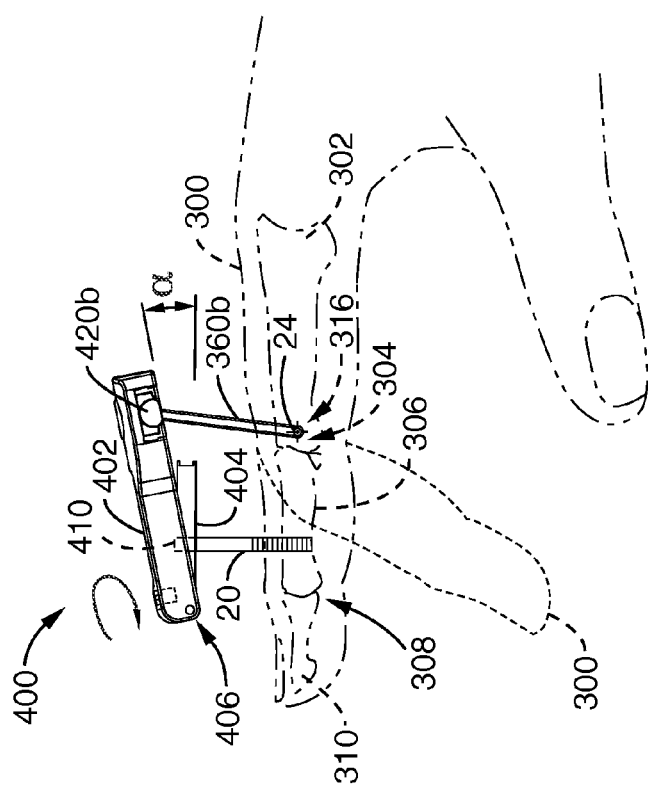
FIG. 37 is a side view of an alternative embodiment of the F3 device shown in FIG. 2 according to the present invention, illustrating the palmar-dorsal adjustability of the device through an angle $\alpha$ to change the tension between the dorsal and transverse pins and further illustrating compliance of the device during flexure of the finger maintaining concentric reduction of the PIP joint.

Referring now to FIG. 37 through FIG. 41, an alternative embodiment 400 of the F3 device is illustrated. FIG. 37 and FIG. 38 illustrate the hand of a subject with the F3 device 400 applied to the index finger 300. The boney anatomy of the index finger is also shown, including the proximal phalanx 302, the PIP joint 304, the middle phalanx 306, the DIP joint 308, and the distal phalanx 310. As is the case with embodiment 12 previously described, the injury being treated is in the PIP joint 304 and the F3 device 400 maintains concentric reduction of the PIP joint 304 while allowing flexure of the finger as shown by the downward extending outline. During flexure of the finger, the PIP joint rotates about its axis of rotation 316.

The F3 device 400 includes first and second longitudinal support members 402, 404 joined at a pivot joint 406, and a transverse arm assembly 408 (see FIG. 41) passing through first support member 402 at the proximal end of the member. The F3 device 400 engages the transverse pin 24 that has been inserted through the PIP joint along the joint axis 314 using elastic bands, only one such band 360b being visible (an identical elastic band is deployed on the opposite side of the transverse arm assembly 408). The F3 device 400 also engages the dorsal pin 20 by receiving the exposed end of the pin 20 through an aperture 410 (see FIG. 39) in the second longitudinal support member 404.

In the embodiment shown, the tension adjustment screw controls the relative position of the first and second longitudinal support members so as to form an angle $\alpha$ that adjusts the tension between dorsal pin 20 and transverse pin 24. Again, as discussed previously, tension can also be adjusted by increasing the number of elastic bands or by using elastic bands with different elasticity factors either alone or in combination with this adjustment. In the preferred embodiments of the invention, once angle $\alpha$ is fixed at a selected angle, that angle remains substantially constant as the PIP joint 304 is flexed. The two support members 402, 404 are of unequal length in the embodiment shown, allowing the second support member 404 to be retracted within the first support member 402 as illustrated in FIG. 38 and FIG. 39. This is a design choice and can be replaced without loss of function by two members of equal length or by two members of different lengths but reversed such that the first (upper) support member is shorter than the second (lower) support member.

Figure 41:
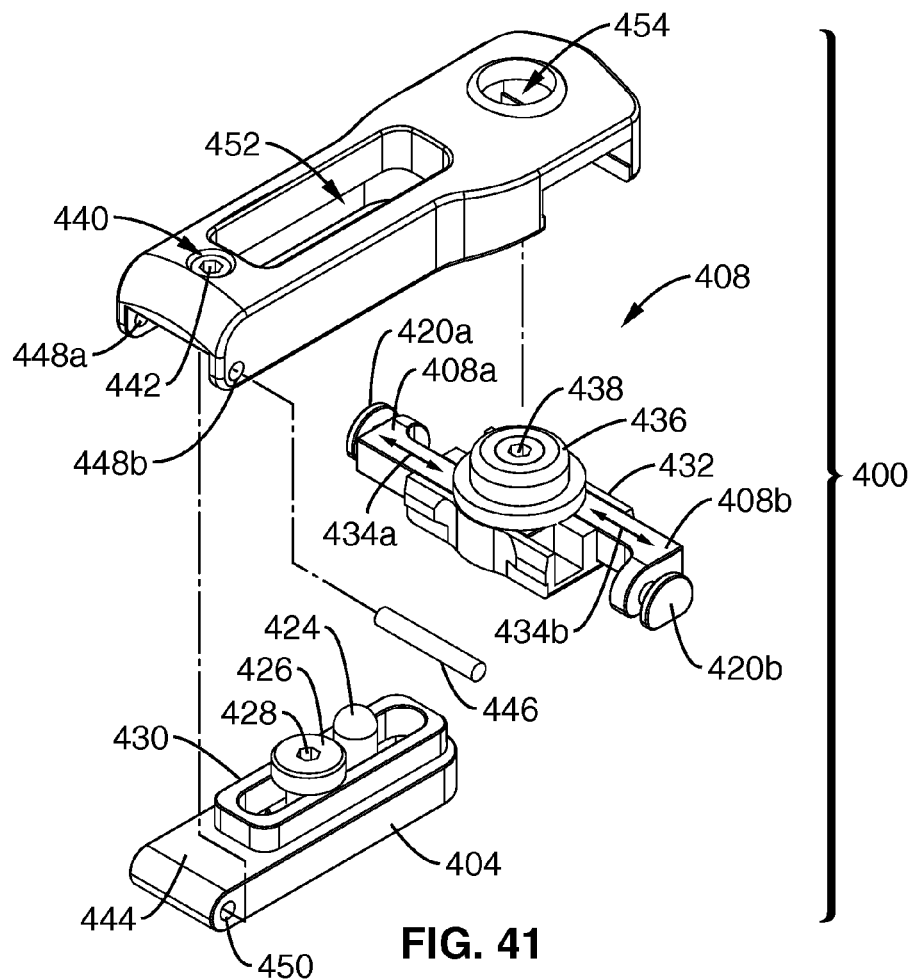
FIG. 41 is a perspective exploded view of the device shown in FIG. 37.

The underside of the F3 device 400 is shown in FIG. 39 with the shorter second longitudinal support member 404 fully retracted within a cavity in the longer first longitudinal support member 402. With the second support member thus fully retracted, the angle α is zero degrees as can also be seen in FIG. 38. As shown, the aperture 410 in the second longitudinal support member 404 is an opening in a sliding block 412 that can be moved longitudinally within an opening 414 in that member along the direction of the arrow 416. Adjustment of the longitudinal position of the block 412 allows the device to accommodate different degrees of spacing between the dorsal and transverse pins, and thus fingers of different lengths. Referring also to FIG. 40 and FIG. 41, once the desired spacing is achieved, a length adjustment lock screw 418 can be tightened to fix the position of the block 412.

The two ends of the transverse arm assembly 408 terminate in knob-shaped tension connectors 420a, 420b. The necks 422a, 422b joining the tension connectors to the remainder of the transverse arm serve as mounts for tension generating elements by forming grooves that can accommodate hooks or loops at the ends of springs, elastic bands, or any comparable tension generating elements. The elastic band 360b shown in FIG. 37, which represents the tension generating element in this embodiment, can thus be looped around one neck 422b while a second, identical elastic band (not shown) is looped around the other neck 422a.

Referring more particularly to FIG. 40 and FIG. 41, surrounding the aperture 410 (FIG. 39) is a post 424 that extends upward through the second support member 404. The length adjustment lock screw 418 (FIG. 39) terminates in a head 426 having a hex socket 428. When lock screw 418 is rotated, head 426 is tightened against the shoulder 430 of second support member 404 and block 412 is drawn up against the inside surface of second support member 404 from which shoulder 430 protrudes, thereby securing the position of the block 412.

The transverse arm assembly 408 comprises two segments 408a, 408b that both rest within a retaining block 432 that allows the two segments to move in opposite directions, along the directions of the arrows 434a, 434b. Although not visible in the figure, a peg extends upward from each of the two segments 408a, 408b toward a width adjustment disk 436 whose underside contains slots (also not shown) to receive the pegs. Rotation of the disk 436 by way of a hexagonal socket 438 in one direction causes the two segments 408a, 408b to draw together, and in the opposite direction to spread apart. The angle α between the two longitudinal support members 402, 404, and hence the tension between the dorsal 20 and transverse 24 pins, is controlled by a set screw 440, also with a hexagonal socket 442. The set screw 440 is threaded into the first longitudinal support member 402 and sets a minimum angle α by contacting the surface 444 of the second support member 404. Pivot joint 406 is formed by a pin 446 extending through apertures 448a, 448b in first longitudinal support member 402 and through a corresponding channel 450 in second longitudinal support member 404. Note also that first longitudinal support member 402 includes a slot 452 for receiving shoulder 430 and an aperture 454 for receiving disk 436.

Figure 42:
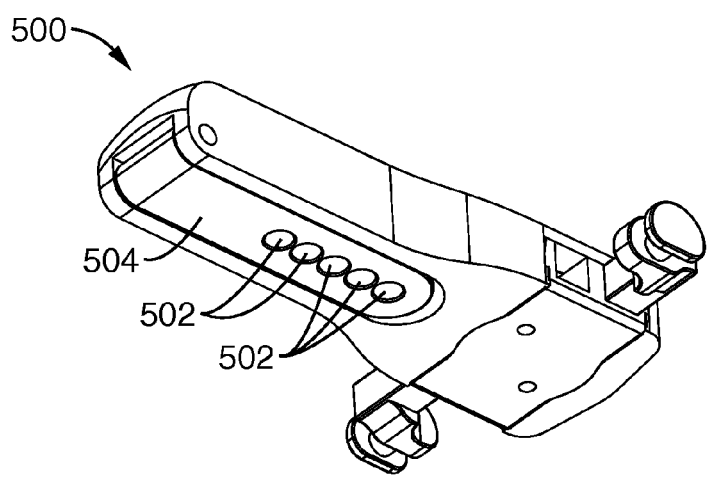
FIG. 42 is a bottom perspective view of an alternative embodiment of the device shown in FIG. 39 with a plurality of apertures for insertion of a dorsal pin to adjust the longitudinal position between the dorsal pin and the transverse pin.
Figure 43:
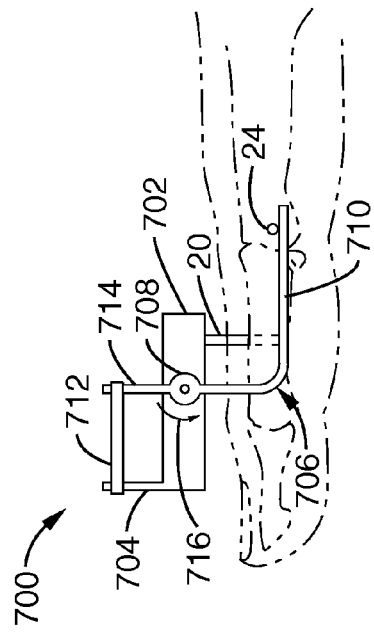
FIG. 43 illustrates a fourth alternative embodiment of an F3 device according to the present invention.
Figure 44:
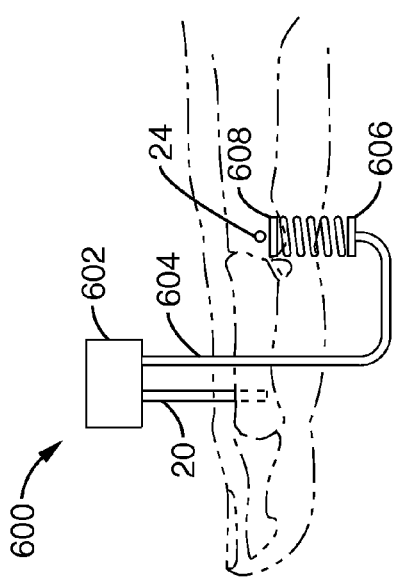
FIG. 44 illustrates a fifth alternative embodiment of an F3 device according to the present invention.
Figure 46:
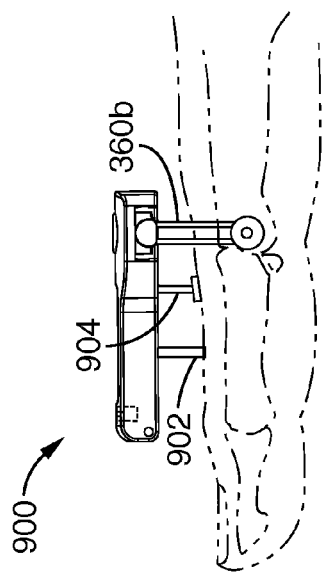
FIG. 46 illustrates a seventh alternative embodiment on an F3 device according to the present invention.

FIG. 42 through FIG. 44 illustrate further embodiments of an F3 device according to the present invention. The F3 device 500 shown in FIG. 42 is substantially the same as the configuration shown in FIG. 37 through FIG. 41 except that the sliding block 412 has been replaced with five apertures 502, that are all fixed in position and longitudinally aligned along a modified short longitudinal bar 504. Different degrees of spacing between the dorsal and transverse pins are achieved by selecting a single aperture among the five apertures shown for use as the aperture to receive the dorsal pin. While FIG. 42 shows five apertures, the number can vary widely from as few as two apertures to greater than five.

Still further alternatives are shown in FIG. 43 through FIG. 46. In FIG. 43, an F3 device 600 comprises a single support member 602 to which two J-shaped rods are mounted, only one of which 604 is visible, each J-shaped rod terminating in a compression spring, only one of which 606 is visible. When the apparatus is deployed, the finger passes between the two J-shaped rods, and the upper ends 608 of the compression springs contact the exposed ends of the transverse pin 24, urging the transverse pin upward (in the palmar-to-dorsal direction). Also mounted to the support member 602 is the dorsal pin 20, and with the placement of the compression springs 606 and the configuration of the J-shaped rods 604, the device simultaneously exerts a downward (dorsal-to-palmar) force on the dorsal pin 20 as it is exerting an upward (palmar-to-dorsal) force on the transverse pin 24.

In FIG. 44 the device 700 comprises a support member 702 with an upwardly extending arm 704 and two L-shaped rods, only one of which 706 is shown, each L-shaped rod being mounted to the support member at a pivot connection 708, and the two L-shaped rods positioned on either side of the finger when the apparatus is deployed. The dorsal pin 20 is mounted to the support member 702, and the two ends of the transverse pin 24 rest on the lower, horizontal legs 710 of the L-shaped rods. An elastic band 712 draws the upper ends of the vertical legs 714 of the L-shaped rods toward the upright arm 704, which exerts a rotary force on the pivot connection 708 in the counterclockwise direction as shown by the arrow 716. This urges the transverse pin 24 upward and the dorsal pin 20 downward.

Figure 45:
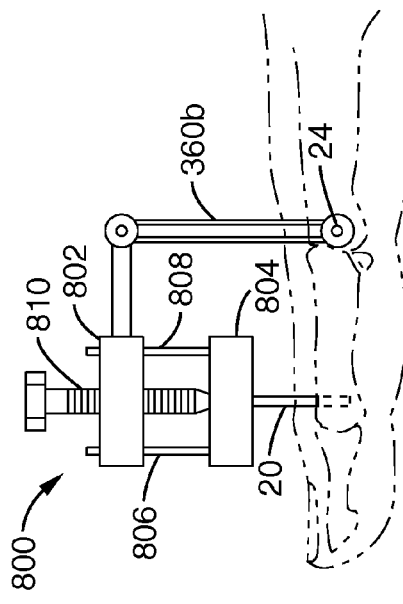
FIG. 45 illustrates a sixth alternative embodiment of an F3 device according to the present invention.

The F3 device 800 shown in FIG. 45 is similar to that of FIG. 1 through FIG. 41, except that instead of using components that are joined at a pivot connection, a pair of parallel support members 802, 804 are joined in a sliding relation by way of parallel rods 806, 808, their spacing being set by a vertical adjustment screw 810. The dorsal pin 20 and the transverse pin 24 are engaged by the device as in the embodiments of FIG. 1 through FIG. 41, and adjustment of the tension applied to the two pins is achieved by changing the vertical spacing between the two blocks rather than by a pivot angle.

In each of the various embodiments described above, the dorsal pin is part of the mechanism of the F3 device that urges the proximal end of the middle phalanx downward; that is, in the dorsal-to-palmar direction. Once the F3 device is fully deployed, the forces on the dorsal pin may in some cases cause the pin to penetrate further into and through the middle phalanx, causing the phalanx to slide upward along the pin. This movement will compromise the downward force that the splint is intended to exert on the phalanx. To prevent this occurrence, the dorsal pin is preferably anchored in the middle phalanx in a manner that will prevent the pin from moving downward through the phalanx. This can be accomplished in various ways.

The preferred approach is to use a threaded dorsal pin as previously described. A less desirable approach would be to use an unthreaded dorsal pin having a shoulder that rests against the skin to limit the depth of penetration. Still another less desirable approach is the F3 device 900 illustrated in FIG. 46 which uses a threaded or unthreaded dorsal pin 902 that is supplemented by a separate footed extension 904 extending from the device.

The following patents and publications which describe methods and devices related to the above disclosure are incorporated herein by reference in their entirety: U.S. Pat. No. 6,063,087; U.S. Pat. No. 6,592,584; U.S. Pat. No. 6,565,563; Agee, J. M., "Unstable fracture dislocations of the proximal interphalangeal joint of the fingers: A preliminary report of a new treatment technique," *J. Hand Surg.* 3(4): 386-389 (July 1978); and Agee, J. M., et al., "Unstable Fracture Dislocations of the Proximal Interphalangeal Joint," *Clin. Orthop.* 214: 101-112 (1985).

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. An apparatus for repositioning the middle phalanx of a finger in relation to the head of the proximal phalanx in said finger where said finger has an associated proximal interphalangeal joint fracture dislocation, comprising:
    a support structure;
    said support structure adapted for coupling to a dorsal pin positioned in said middle phalanx of said finger;
    said support structure adapted for coupling to a single transverse pin positioned in said proximal phalanx of said finger; and
    a biasing member coupled to the support structure, the biasing member and support structure configured to exert a force between said dorsal and transverse pins to simultaneously translate the dorsal pin in an opposing direction relative to the transverse pin, which simultaneously translates the proximal end of the middle phalanx in a palmar direction and the head of the proximal phalanx in a dorsal direction.

2. An apparatus as recited in claim 1, wherein said support structure comprises:
    a first support member; and
    a second support member pivotally coupled to said first support member;
    said first and second support members adapted for relative articulation through an angle.

3. An apparatus as recited in claim 2, comprising:
    said first and second support members joined to each other by an adjustable pivotable connection for orienting said support members with an adjustable spacing therebetween along a direction defined as a vertical direction;
    first and second tension connectors coupled to said first support member and spaced from each other along a direction that is transverse to said vertical direction and which is defined as a first horizontal direction; and
    one or more apertures in said second support member for receiving said dorsal pin in an orientation substantially parallel to said vertical direction and spaced apart from said first and second tension connectors along a second horizontal direction that is substantially perpendicular to both said vertical direction and said first horizontal direction;
    whereby said adjustable pivotable connection is configured to adjust the position of said first and second tension connectors along said vertical direction relative to said one or more apertures.

4. An apparatus as recited in claim 3, further comprising rotary drive on said first support member for adjusting the spacing of said first and second tension connectors along said first horizontal direction.

5. An apparatus as recited in claim 4, further comprising:
    a U-shaped rod of resilient construction having two arms, each arm terminating on one of said first and second tension connectors; and
    a pair of spreaders coupled to said arms for applying an adjustable spreading force to said arms.

6. An apparatus as recited in claim 5, wherein said rotary drive on said first support member is operatively coupled to said spreaders.

7. An apparatus as recited in claim 3, further comprising a proximal-distal adjustment mechanism for adjusting the spacing along said second horizontal direction between said one or more apertures and said first and second tension connectors.

8. An apparatus as recited in claim 7:
    wherein said proximal-distal adjustment mechanism comprises a block slidably mounted to said second support member; and
    wherein said one or more apertures are located in said block.

9. An apparatus as recited in claim 7, wherein said one or more apertures comprises a plurality of apertures in said second support member at different distances from said first and second tension connectors along said second horizontal direction.

10. An apparatus as recited in claim 3, further comprising:
    said transverse pin;
    said dorsal pin; and
    first and second elastic bands;
    each said elastic band sized to loop around one end of said transverse fixation pin and one of said first and second tension connectors.

11. An apparatus as recited in claim 10:
    wherein said transverse pin is unthreaded; and
    wherein said dorsal pin is threaded.

12. An apparatus as recited in claim 3:
    wherein said first and second support members are joined to each other by a pivot joint to form an angle; and
    wherein said pivot joint is configured to allow for adjusting said angle.

13. An apparatus as recited in claim 3, wherein said first and second tension connectors comprise grooves adapted to engage elastic bands.

14. An apparatus as recited in claim 3, wherein said first and second tension connectors comprise hooks adapted to engage elastic bands.

15. An apparatus as recited in claim 3, further comprising means for limiting the depth to which said dorsal pin received by said pin receiving means penetrates said middle phalanx.

16. An apparatus as recited in claim 3, further comprising first and second elastic bands to be engaged by said first and second tension connectors, respectively.

17. An apparatus as recited in claim 2, wherein the biasing member comprises a tension generating element, the apparatus further comprising:
a transverse arm assembly coupled to said first support member;
the pair of tension connectors coupled to said transverse arm assembly;
each said tension connector adapted for coupling a tension generating element to said support structure;
said second support member adapted for coupling to said dorsal pin positioned in said middle phalanx of said finger.

18. An apparatus as recited in claim 17, further comprising:
a screw adjustment mechanism for adjusting the relative angle between the first and second support members.

19. An apparatus as recited in claim 17:
wherein said transverse arm assembly comprises first and second segments slidably coupled to said first support member; and
a screw adjustment mechanism coupled to said first and second segments for adjusting relative distance between said tension connectors.

20. An apparatus as recited in claim 17, wherein said second support member includes a plurality of apertures for receiving said dorsal pin and accommodating different degrees of spacing between the dorsal and transverse pins.

21. An apparatus as recited in claim 17, further comprising a transverse pin, a dorsal pin, and first and second elastic bands, each said elastic band sized to loop around one end of said transverse pin and one of said tension connectors.

22. An apparatus as recited in claim 2, comprising:
said biasing member comprising first and second tension generating elements;
a U-shaped rod coupled to at least one of said support members;
said rod having a pair of arms with a tension connector at an end of each arm;
each said tension connector adapted for-receiving one of the first and second tension generating elements;
said second support member adapted for coupling to said dorsal pin positioned in said middle phalanx of said finger.

23. An apparatus as recited in claim 22, further comprising:
a pair of spreaders;
said spreaders having outer ends with slots for receiving said arms of said rod;
said spreaders having arms slidably coupled to said first support member;
wherein relative distance between the outer ends of said spreaders is adjustable by a screw adjustment mechanism.

24. An apparatus as recited in claim 22, wherein said second support member includes a plurality of apertures for receiving said dorsal pin and accommodating different degrees of spacing between the dorsal and transverse pins.

25. An apparatus as recited in claim 22, further comprising said transverse pin, said dorsal pin, and first and second elastic bands, each said elastic band sized to loop around one end of said transverse pin and one of said tension connectors.

26. An apparatus as recited in claim 1:
wherein said support structure comprises first and second support members joined to each other by an adjustable slideable connection for orienting said support members with an adjustable spacing therebetween along a direction defined as a vertical direction;
wherein said apparatus further comprises:
first and second tension connectors coupled to said first support member and spaced from each other along a direction that is transverse to said vertical direction and which is defined as a first horizontal direction; and
an aperture in said second support member for receiving said dorsal pin in an orientation substantially parallel to said vertical direction and spaced apart from said first and second tension connectors along a second horizontal direction that is substantially perpendicular to both said vertical direction and said first horizontal direction;
whereby said adjustable slideable connection is configured to adjust the position of said first and second tension connectors along said vertical direction relative to said pin receiving means; and
wherein said first and second support members are joined to each other by a spacer of adjustable length.

27. An apparatus as recited in claim 1, wherein the support structure and the biasing member are configured to allow the middle phalanx to move in extension and flexion with respect to the proximal phalanx while said force is being exerted.

28. An apparatus for repositioning the middle phalanx of a finger in relation to the head of the proximal phalanx in said finger where said finger has an associated proximal interphalangeal joint fracture dislocation, comprising:
a support structure;
said support structure adapted for coupling to a dorsal pin positioned in said middle phalanx of said finger;
said support structure adapted for coupling to a single transverse pin positioned in said proximal phalanx of said finger; and
a biasing member coupled to the support structure, the biasing member and support structure configured to exert a force between said dorsal and transverse pins to obtain reduction of the proximal interphalangeal joint fracture dislocation.

29. An apparatus as recited in claim 28, wherein the support structure and the biasing member are configured to allow the middle phalanx to move in extension and flexion with respect to the proximal phalanx while said force is being exerted.

* * * * *